US010398400B2

(12) United States Patent
Kim

(10) Patent No.: US 10,398,400 B2
(45) Date of Patent: Sep. 3, 2019

(54) RADIOGRAPHIC IMAGING APPARATUS AND METHOD FOR CONTROLLING THE SAME

(71) Applicant: Samsung Electronics Co., Ltd., Gyeonggi-do (KR)

(72) Inventor: Sang Uk Kim, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 349 days.

(21) Appl. No.: 15/299,377

(22) Filed: Oct. 20, 2016

(65) Prior Publication Data

US 2017/0172535 A1   Jun. 22, 2017

(30) Foreign Application Priority Data

Dec. 17, 2015 (KR) ........................ 10-2015-0181046

(51) Int. Cl.
*A61B 6/00* (2006.01)
*A61B 6/03* (2006.01)
*A61B 6/06* (2006.01)

(52) U.S. Cl.
CPC .............. *A61B 6/544* (2013.01); *A61B 6/032* (2013.01); *A61B 6/06* (2013.01); *A61B 6/4291* (2013.01); *A61B 6/461* (2013.01); *A61B 6/465* (2013.01); *A61B 6/467* (2013.01); *A61B 6/502* (2013.01); *A61B 6/545* (2013.01); *A61B 6/56* (2013.01); *A61B 6/4464* (2013.01)

(58) Field of Classification Search
None
See application file for complete search history.

(56) References Cited

U.S. PATENT DOCUMENTS

2008/0101538 A1   5/2008   Schliermann
2014/0009573 A1*  1/2014   Fujita ...................... A61B 6/14
                                                                    348/36

* cited by examiner

*Primary Examiner* — Hoon K Song

(57) ABSTRACT

A radiographic imaging apparatus and a method for controlling the same. The radiographic imaging apparatus includes a database configured to store first subject information and an imaging condition corresponding to the first subject information A controller, upon receiving second subject information regarding a subject to be image, is configured to detect an imaging condition corresponding to second subject information acquired from the database, determine a recommended imaging condition using the detected imaging condition, and determine reliability of the recommended imaging condition. A user interface (UI) is configured to display the recommended imaging condition and the reliability of the recommended imaging condition.

16 Claims, 19 Drawing Sheets

| INDEX | AGE | SEX | RACE | HEIGHT | THICKNESS | SHOULDER WIDTH | KVp | mAs | EI |
|---|---|---|---|---|---|---|---|---|---|
| 1 | 27 | M | M | 178 | 21 | 46 | A1 | B1 | C1 |
| 2 | 43 | F | M | 163 | 21 | 38 | A2 | B2 | C2 |
| 3 | 41 | F | M | 165 | 22 | 35 | A3 | B3 | C3 |
| 4 | 35 | M | M | 185 | 23 | 55 | A4 | B4 | C4 |
| ... | ... | ... | ... | ... | ... | ... | ... | ... | ... |

611 — row 1
612 — row 2
613 — row 3
614 — row 4

| INDEX | AGE | SEX | RACE | HEIGHT | THICKNESS | SHOULDER WIDTH | KVp | mAs | EI |
|---|---|---|---|---|---|---|---|---|---|
| 1 | 27 | M | M | 178 | 21 | 46 | A1 | B1 | C1 |
| 2 | 43 | F | M | 163 | 21 | 38 | A2 | B2 | C2 |
| 3 | 41 | F | M | 165 | 22 | 35 | A3 | B3 | C3 |
| 4 | 35 | M | M | 185 | 23 | 55 | A4 | B4 | C4 |
| ... | ... | ... | ... | ... | ... | ... | ... | ... | ... |

611 — 612 — 613 — 614

RADIOGRAPHIC IMAGING APPARATUS AND METHOD FOR CONTROLLING THE SAME

CROSS-REFERENCE TO RELATED APPLICATION(S) AND CLAIM OF PRIORITY

The present application is related to and claims the benefit of Korean Patent Application No. 10-2015-0181046, filed on Dec. 17, 2015 in the Korean Intellectual Property Office, the disclosure of which is incorporated herein by reference.

TECHNICAL FIELD

Embodiments of the present disclosure relate to a radiographic imaging apparatus and a method for controlling the same.

BACKGROUND

A radiographic imaging apparatus is an imaging system that emits radiation (such as X-rays) to a subject (such as a human body or an article) to acquire an internal image of the subject, such that the acquired image is supplied to users of the radiographic imaging apparatus. For example, the users may include doctors, nurses, medical technologists, radiologists, medical image specialists, security guards, etc. The user may intuitively recognize internal tissues or structures of the subject using the image acquired by the radiographic imaging apparatus. The radiographic imaging apparatus may acquire an internal image of the subject using unique properties (e.g., density) of materials constituting the subject. In more detail, when radiation is applied to the subject, the radiation is absorbed and attenuated by the subject or passes through the subject according to unique characteristics of materials or structures within the subject, such that the radiographic imaging apparatus may acquire the internal image of the subject. For example, the radiographic imaging apparatus emits radiation to a subject, such as a human body, receives radiation transmitted through the subject or directly transmitted through the surroundings of the subject, converts the received radiation into an electrical signal, and generates a radiographic image using the converted electrical signal, thereby acquiring a radiographic image indicating internal tissues, structures, or materials within the subject.

For example, the radiographic imaging apparatuses include a digital radiography (DR) apparatus, a full field digital mammography (FFDM) apparatus, a computed tomography (CT) apparatus, etc. Radiographic imaging apparatuses have been widely used in various industries, for example, healthcare, security system, construction, etc.

SUMMARY

To address the above-discussed deficiencies, it is a primary object to provide a radiographic imaging apparatus for allowing a user to properly establish necessary radiographic imaging conditions, and a method for controlling the same.

It is another aspect of the present disclosure to provide a radiographic imaging apparatus for providing not only a recommended value that allows a user to properly select intensity or dose of radiation (e.g., X-rays) but also reliability of the recommended value, and a method for controlling the radiographic imaging apparatus.

Additional aspects of the disclosure will be set forth in part in the description which follows and, in part, will be obvious from the description, or may be learned by practice of the disclosure.

Various embodiments of the present disclosure are directed to providing a radiographic imaging apparatus and a method for controlling the same that substantially obviate one or more problems due to limitations and disadvantages of the related art.

In accordance with one aspect of the present disclosure, a radiographic imaging apparatus may comprise a database configured to store first subject information and an imaging condition corresponding to the first subject information, a controller, upon receiving second subject information regarding a subject to be image, configured to detect an imaging condition corresponding to second subject information acquired from the database, determine a recommended imaging condition using the detected imaging condition, and determine reliability of the recommended imaging condition; and a user interface (UI) configured to display the recommended imaging condition and the reliability of the recommended imaging condition.

The controller may be configured to determine at least one of the recommended imaging condition and the reliability of the recommended imaging condition on the basis of first subject information corresponding to the detected imaging condition, or determine at least one of the recommended imaging condition and the reliability of the recommended imaging condition on the basis of a difference between the first subject information corresponding to the detected imaging condition and the second subject information.

The controller may be configured to determine at least one of the recommended imaging condition and the reliability of the recommended imaging condition on the basis of a relationship between the first subject information and transmittance, or determine at least one of the recommended imaging condition and the reliability of the recommended imaging condition on the basis of a difference between transmittance and a difference between the first subject information and the second subject information.

The transmittance may include a ratio between a dose of radiation acquired before the radiation passes through the subject and a dose of radiation having passed through the subject.

The controller may be configured to acquire a target transmittance further using the second subject information, or acquire a target transmittance on the basis of a difference between the first subject information and the second subject information, thereby determining the recommended imaging condition from the acquired target transmittance.

The imaging condition corresponding to the first subject information includes radiation strength, and the recommended imaging condition may include a recommended dose of radiation and the controller may be configured to acquire a recommended dose of radiation using the target transmittance and the radiation strength corresponding to the first subject information.

The controller may acquire the recommended dose of radiation further using a filter correction value.

The controller may be configured to acquire a predicted error regarding the target transmittance on the basis of the relationship between the first subject information and the transmittance, or acquire a predicted error regarding the target transmittance on the basis of the relationship between the transmittance and the difference between the first subject information and the second subject information, thereby determining the reliability of the recommended imaging condition.

The controller may be configured to perform regression analysis on the basis of the first subject information and the transmittance or perform regression analysis on the basis of the transmittance and the difference between the first subject information and the second subject information, thereby determining the relationship between the transmittance and the difference between the first subject information and the second subject information.

The user interface (UI) may be configured to display the reliability of the recommended imaging condition using at least one of letters, numbers, symbols, and figures.

The user interface (UI) may be configured to display the reliability of the recommended imaging condition in a discrete manner.

The imaging condition may include at least one of radiation strength, radiation dose, an exposure index (EI), and an entrance skin exposure (ESE).

At least one of the first subject information and the second subject information may include at least one of age, sex, race of the subject, length of the subject, thickness of the subject, and width of the subject.

The radiographic imaging apparatus may further comprise at least one of: a subject information collector configured to image a subject so as to measure at least one of length of a subject, thickness of the subject, and width of the subject; and a subject information input module configured to receive at least one of length of a subject, thickness of the subject, and width of the subject.

The controller, when a radiographic imaging request is input, when relative positions of a radiation emitter and a radiation detector are changed, or when the second subject information is changed, may be configured to determine the recommended imaging condition and the reliability of the recommended imaging condition.

The radiographic imaging apparatus may further comprise an imaging condition change input module configured to change the recommended imaging condition.

A method for controlling a radiographic imaging apparatus may comprise acquiring second subject information regarding a subject to be imaged, detecting an imaging condition corresponding to the second subject information from a database for storing first subject information and an imaging condition corresponding to the first subject information, determining a recommended imaging condition and reliability of the recommended imaging condition using the detected imaging condition and displaying the recommended imaging condition and the reliability of the recommended imaging condition.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIG. 7 illustrates a view of examples of subject-related information (hereinafter referred to as subject information) and various imaging conditions stored in a database;

FIG. 8 illustrates a view of an example for detecting an imaging condition corresponding to second subject information obtained from the database;

DETAILED DESCRIPTION

Figure 1:
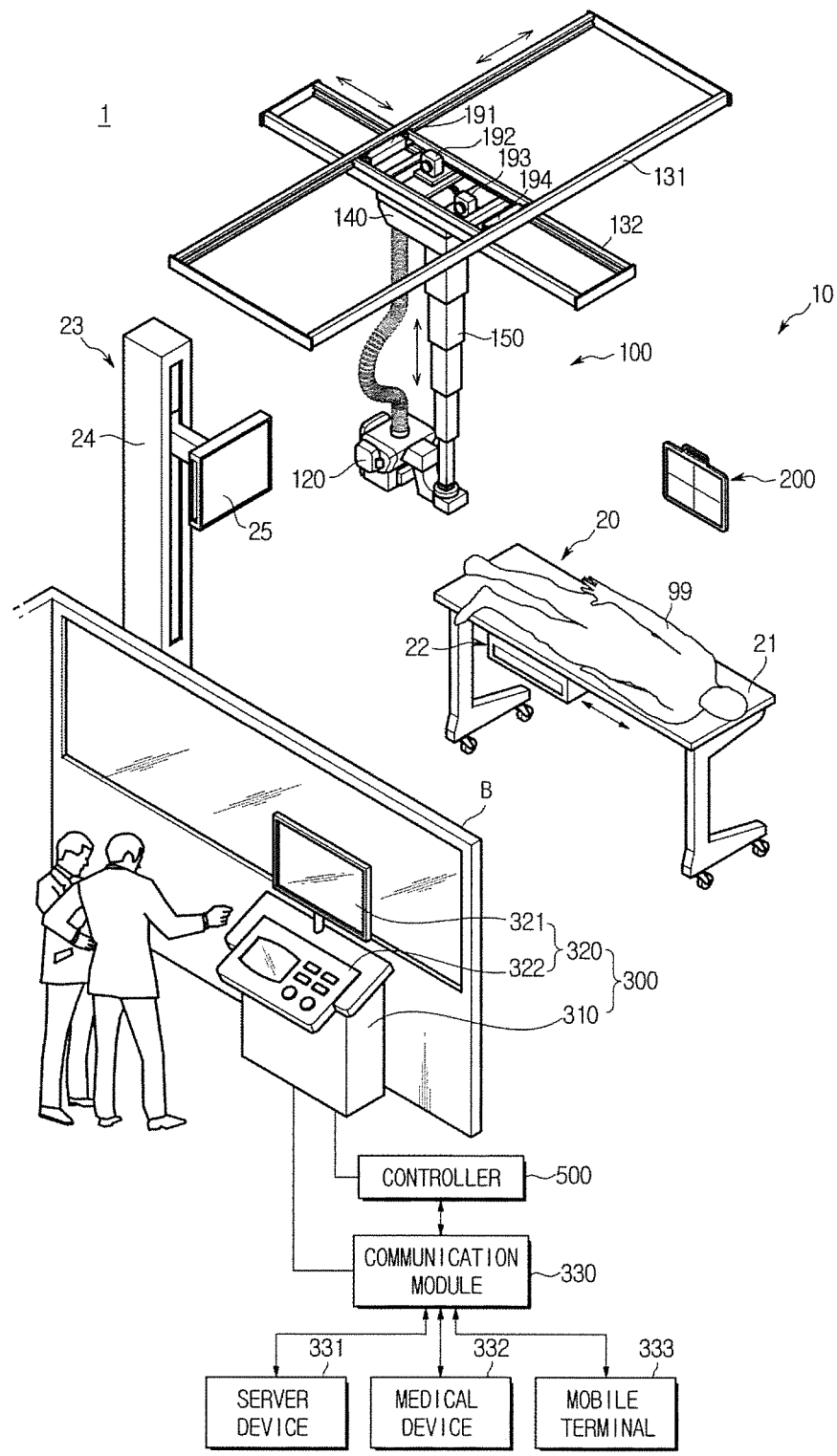
FIG. 1 illustrates a view of a radiographic imaging apparatus according to an embodiment of the present disclosure.

FIGS. 1 through 19, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged radiographic imaging apparatus.

Reference will now be made in detail to the embodiments of the present disclosure, examples of which are illustrated in the accompanying drawings, wherein like reference numerals refer to like elements throughout. A radiographic imaging apparatus according to embodiments of the present disclosure will hereinafter be described with reference to FIGS. 1 to 15.

FIG. 1 illustrates a view of a radiographic imaging apparatus according to an embodiment of the present disclosure.

Referring to FIG. 1, the radiographic imaging apparatus 1 may include a radiographic imaging module 10 and a computer device 300 communicably connected to the radiographic imaging module 10.

The radiographic imaging module 10 may be provided to perform radiographic imaging of a subject 99. In more detail, the radiographic imaging module 10 may include a radiation emitter 100 to emit radiation, and a radiation detector 200 to detect radiation. In this case, the subject 99 may include, for example, humans, animals, plants, luggage, etc. The subject 99 may further include animate or inanimate objects, the insides of which are imaged by radiation.

The radiographic imaging module 10 may be implemented in a structure in which the radiation emitter 100 is fixed to the ceiling of an inspection room, or may be implemented in a C-arm structure in which the radiation emitter 100 and the radiation detector 200 are installed. The radiographic imaging module 10 may be implemented in various ways according to categories of the radiographic imaging apparatus 1.

If the radiation emitter 100 is fixed to the ceiling of an inspection room, the radiation emitter 100 may include a plurality of rails (131, 132) to move a moving carriage 140 in a horizontal direction, a post frame 150 formed to be elongated or shortened in length, and a radiation emission module 120 in which constituent elements of the radiation emitter 100 are embedded.

The radiation emission module 120 may include various constituent elements related to the radiation emitter 100. The radiation emission module 120 may be movable in various directions using the plurality of rails (131, 132) and the post frame 150. In this case, the radiation emission module 120 may move the moving carriage 140 in the direction along which the rails (131, 132) are installed using a wheel connected to at least one motor (191 to 194), such that the radiation emission module 120 may horizontally move to a specific position. An encoder may be installed in each of the motors (191 to 195), and the controller 500 may also determine the position of the radiation emission module 120 or the presence or absence of change in the position of the radiation emission module 120 on the basis of revolutions per minute (RPM) of a motor measured by the encoder. The radiation emission module 120 may also vertically move through extension or reduction of the post frame 150.

The radiographic imaging module 10 may further include at least one of an imaging table 20 and an imaging stand 23, each of which is connected to the radiation detector 200. The imaging table 20 and the imaging stand 23 may be fixed to a specific position of the indoor space of a radiographic imaging room, or may be movable within the radiographic imaging room. The imaging table 20 may include a support plate 21 on which the subject 99 is laid, and a first radiation detector mounting module 22 detachably connected to the radiation detector 200. The imaging stand 23 may include a post 24, and a second radiation detector mounting module 25 detachably connected to the radiation detector 200.

The computer device 300 may receive various commands or data from the user, or may provide the user with radiographic images acquired by radiation. In addition, the computer device 300 may display various graphical user interfaces (GUIs) related to control of the radiographic imaging module 10 so as to provide the user with the GUIs.

The computer device 300 may include a main body 310 and a user interface (UI) connected to the main body 310. In more detail, at least one of a display 321 and an input module 322 may be connected to the main body 310 through a cable or a wireless communication network such that data or commands can be communicated between the main body 310 and the at least one of the display 321 and the input module 322. A user command entered through the input module 322 may be transferred to the main body 310, and various images acquired by the main body 310 may be displayed on the display 321. The main body 310 may include a controller 500.

The controller 500 may transmit various kinds of information to a server device 331, another medical device 332, and a mobile terminal 333 using a communication module 330, or may receive various kinds of information or commands from the server device 331, the medical device 332, and the mobile terminal 333. A detailed description of the controller 500 is as follows. The communication module may communicate with the main body 310 and other devices (331 to 333) through a wired communication network or a wireless communication network.

The radiographic imaging module 10 may be installed in the radiographic imaging room, and may be installed in a separate space separated from the radiographic imaging room by a barrier B, such that an operator (or administrator) of the radiographic imaging apparatus 1 may perform radiographic imaging of the subject 99 without being exposed to radiation.

The radiographic imaging module 10 and the computer device 300 may communicate with each other through a wired or wireless communication network. In this case, the wired communication network may be implemented using various kinds of cables. The wireless communication network may be implemented using at least one of a local area network (LAN) communication protocol and a mobile communication protocol.

Figure 2:
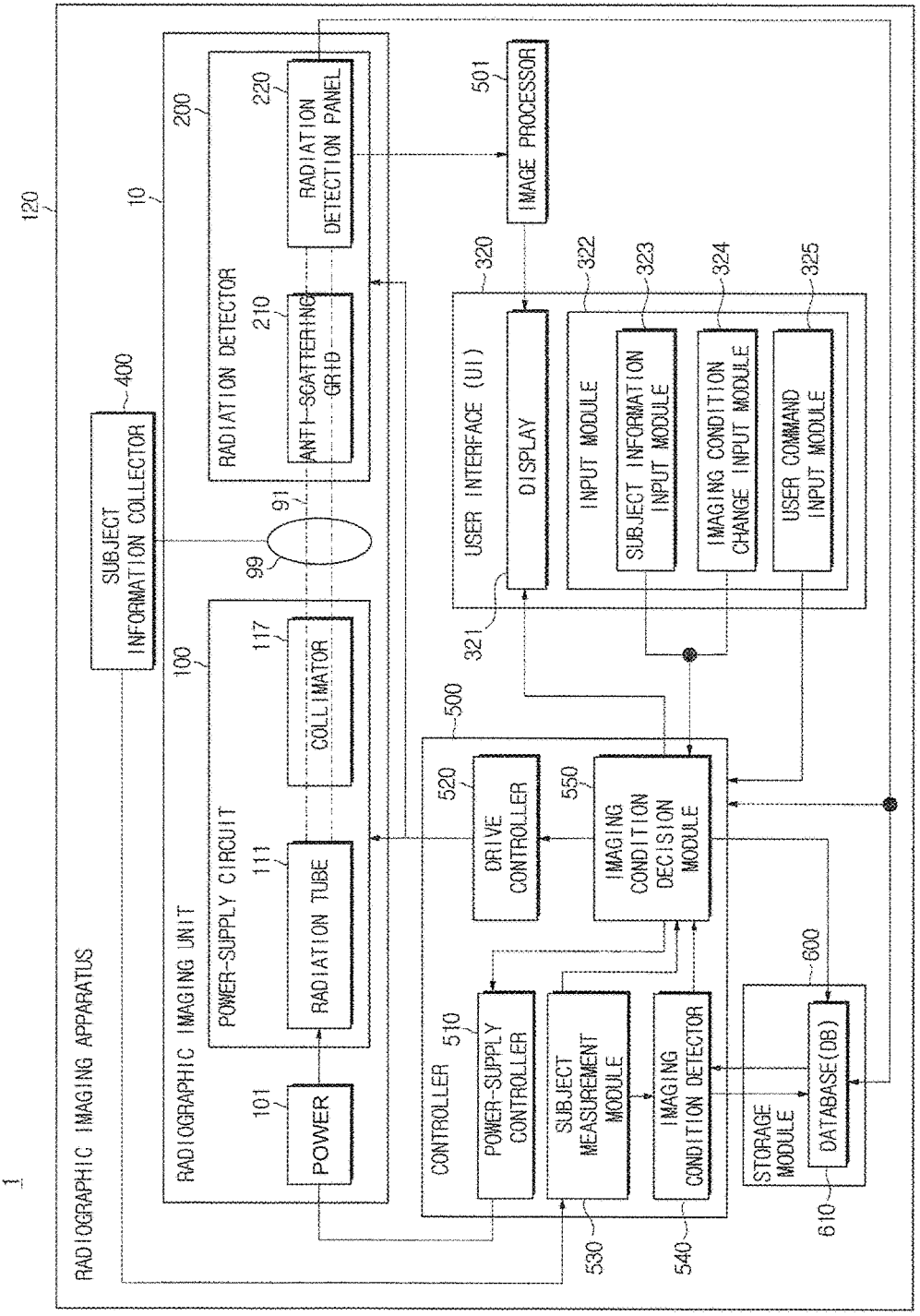
FIG. 2 illustrates a control block diagram for a radiographic imaging apparatus according to an embodiment of the present disclosure.

FIG. 2 illustrates a control block diagram illustrating a radiographic imaging apparatus according to an embodiment of the present disclosure.

Referring to FIG. 2, the radiographic imaging apparatus 1 may include a radiographic imaging module 10, a user interface (UI) 320, a controller 500, an image processor 501, and a storage module 600.

The radiographic imaging module 10 may include a power-supply module 101, a radiation emitter 100, and a radiation detector 200. The power-supply module 101 may provide electric energy to respective components of the radiographic imaging module 10. For example, the power-supply module 101 may output electric energy having a predetermined tube voltage and a predetermined tube current to the radiation tube 111 of the radiation emitter 100. Upon receiving the predetermined tube voltage and the predetermined tube current from the power-supply module 101, the radiation emitter 100 may emit radiation (91 in FIG. 2) to the subject 99. The radiation detector 200 may receive radiation 91 having passed through the subject 99, or may receive radiation that is directly transferred to the radiation detector 200 without passing through the subject 99. The radiation detector 200 may output an electrical signal corresponding to the received radiation 91 to the image processor 501.

The power-supply module 101, the radiation emitter 100, and the radiation detector 200 will hereinafter be described in detail.

The image processor 501 may generate a radiographic image to be viewed by user's eyes upon receiving an electrical signal from the radiation detection panel 220. The image generated by the image processor 501 may include still images and moving images. In this case, the moving image may be implemented by the display 321 configured to sequentially display two or more still images. In addition, the image processor 501 may further perform various kinds of image processing on the generated radiographic image as necessary. For example, the image processor 501 may sharpen all or some of the generated radiographic image using a high pass filter (HPF), or may blur all or some of the radiographic image using a low pass filter (LPF). In another example, the image processor 501 may generate a stereoscopic image on the basis of the plurality of generated radiographic images, or may add desired colors to the generated radiographic images according to a predefined rule. The image processor 501 may further perform various image processing according to selection of a system designer. The image processor 501 may transmit the generated or processed images to at least one of the controller 500 and the display 321 of the user interface (UI) 320.

The controller 500 may control overall operation of the radiographic imaging apparatus 1. For example, the controller 500 may control at least one of the radiation emitter 100 and the power-supply module 101 such that a predetermined dose of radiation 91 having predetermined intensity may be emitted to the subject 99. In addition, the controller 500 may control the display 321 of the user interface 302 to display a predetermined image. In this case, the predetermined image may include at least one of symbols, letters, numbers, shapes, formats, and colors.

In accordance with one embodiment, the controller 500 may include a power-supply controller 510 configured to control the power-supply module 101; a drive controller 520 configured to control the driving operation (e.g., position movement or rotation of the radiation emitter 100 and the radiation detector 200 of the radiographic imaging module 10); a subject measurement module 530 configured to measure at least one of length, width, and thickness of the subject 99; an imaging condition detector 540 configured to detect not only subject information regarding a subject that is substantially identical or similar to the subject 99 to be imaged from among the legacy imaged subjects, but also the imaging condition; and an imaging condition decision module 550 configured to detect a recommended imaging condition indicating the optimum imaging condition using the detected imaging condition or to establish the imaging condition according to user manipulation. In this case, subject information may include at least one of various numerical values (e.g., age, sex, race, height, thickness, and width of the subject). Besides, the subject information may include various numerical values that may be needed for radiographic imaging and may be considered by the designer. The imaging condition may include at least one of radiation intensity, dose of radiation, an exposure index (EI), and an entrance skin exposure (ESE). If necessary, the imaging condition may include various conditions that may be needed for radiographic imaging and may be considered by the designer.

The power-supply controller 510, the drive controller 520, the subject measurement module 530, the imaging condition detector 540, and the imaging condition decision module 550 may be logically or physically separated from one another. If the above-mentioned constituent components (510, 520, 530, 540, 550) are logically separated from one another, the respective constituent components (510, 520, 530, 540, 550) may be implemented by at least one or at least two semiconductor chips or associated components.

The power-supply controller 510, the drive controller 520, the subject measurement module 530, the imaging condition detector 540, and the imaging condition decision module 550 will hereinafter be described in detail.

The controller 500 and the image processor 501 may be implemented by a semiconductor chip and associated components embedded in the main body 310 of the above-mentioned computer device 300, or may be implemented by the semiconductor chip and associated components embedded in the radiographic imaging module 10. The controller 500 and the image processor 501 may also be provided in the server device 331 separately installed. In accordance with one embodiment, the controller 500 and the image processor 501 may be implemented by the same semiconductor chips and associated components, or may be implemented by different semiconductor chips and associated components. In addition, according to one embodiment, each of the controller 500 and the image processor 501 may be implemented by a single semiconductor chip and associated components, or may be implemented by a plurality of semiconductor chips and associated components.

The storage module 600 may store various kinds of information related to operations of the radiographic imaging apparatus 1, or may store images acquired by the image processor 501. In accordance with one embodiment, the storage module 600 may store a database 610 that includes information regarding at least one subject information and the imaging condition established when the at least one subject is imaged.

The database 610 may be implemented by operations of the radiographic imaging apparatus 1. Alternatively, after the database 610 is generated by a separate device, for example, another radiographic imaging apparatus, the database 610 may be applied to the radiographic imaging apparatus 1 and stored in the storage module. Although the database 610 stored in the storage module 600 is generated by a separate device, the radiographic imaging apparatus 1 may also update the stored database 610. A detailed description of the database 610 is as follows.

The storage module 600 may temporarily and/or non-temporarily store data therein. The storage module 600 may be implemented using at least one of a magnetic disk storage device, a magnetic tape storage device, and a semiconductor storage device. The storage module 600 may also be implemented by various media capable of storing data therein.

The storage module 600 may be installed in the main body 310 of the computer device 300, and may be installed outside the computer device 300 so as to communicate with the computer device 300 through a cable or the like.

The user interface (UI) 320 may provide the user with various graphical user interfaces (GUIs) related to the radiographic image or control of the radiographic imaging module 10, or may receive various command related to the radiographic imaging apparatus 1 from the user.

The user interface 320 may include at least one of a display 321 to display the radiographic image and an input module 322 to receive various commands or data from the user.

For example, the display 321 may be implemented by a cathode ray tube (CRT) or various kinds of display panels. For example, the display panel may be implemented using a liquid crystal display (LCD) panel, a light emitting diode (LED), a display panel, etc. In accordance with one embodiment, the display 321 may be implemented as a touchscreen. In this case, the display 321 may also perform the same functions as in the input module 322. The display 321 may output a graphic object for guiding user's touch manipulation.

The input module 322 may output an electrical signal corresponding to the user manipulation, and may transmit the electrical signal to the second controller 601, such that the computer device 300 may receive user-desired commands. The input module 322 may be implemented by various physical buttons (such as a keyboard device), a knob, a stick-type manipulator, a keyboard, a mouse, a jog dial, a trackball, a track pad, a touchpad, etc., without being limited thereto.

In accordance with one embodiment, the input module 322 may include a subject information input module 323, an imaging condition change input module 324, and a user command input module 325. The subject information input module 323 may receive various kinds of information regarding the subject 99 to be imaged, or may change pre-entered subject 99 associated information. The imaging condition change input module 324 may change the recommended imaging condition. The user command input module 325 may be designed to receive various user commands. In this case, various information regarding the subject 99 may include, for example, the length (or height) of the subject 99, thickness of the subject 99, width of the subject 99, etc.

The subject information input module 323, the imaging condition change input module 324, and the user command input module 325 may be implemented by different input modules or may be implemented by the same input module. In addition, at least two of the subject information input module 323, the imaging condition change input module 324, and the user command input module 325 may also be implemented by different input modules. For example, the subject information input module 323 may be implemented as a keyboard, the imaging condition change input module 324 may be implemented as a mouse or touchscreen for moving a cursor displayed on the display 321, and the user command input module 325 may be implemented as a combination of the keyboard and the mouse. Besides, the subject information input module 323, the imaging condition change input module 342, and the user command input module 325 may be implemented in various ways that can be easily appreciated by a system designer.

In accordance with one embodiment, the radiographic imaging apparatus 1 may further include a subject information collector 400 to measure the subject 99.

The subject information collector 400 may collect various kinds of information related to size measurement of the subject 99 located in the vicinity of the radiation detector 200 using visible light, infrared light, ultrasonic waves, etc.

In accordance with one embodiment, the subject information collector 400 may collect visible light using an imaging unit (such as a camera) that collects visible light and obtains images corresponding to the collected visible light. In this case, the camera may collect visible light reflected from the subject 99, and may obtain a predetermined image corresponding to the collected visible light, such that the camera may capture or image the subject 99. The image captured by the subject information collector 400 may be transferred to the subject measurement module 530 of the controller 500, and the subject measurement module 530 of the controller 500 may measure at least one of length, width, and thickness of the subject 99 to be imaged using the captured image. For example, the subject information collector 400 may include a lens configured to focus light so as to acquire images, an image capturing element configured to record light transmitted through the lens, and various components to assist operations of the lens and the image capturing element. In this case, the image capturing element may be realized by a charge coupled device (CCD), a complementary metal oxide semiconductor (CMOS), etc. Of course, according to one embodiment, the image capturing element may also be implemented by various elements configured to convert light into electrical signals.

In addition, the subject information collector 400 may generate visible light, infrared light, or ultrasonic waves, may emit the visible light, the infrared light, or the ultrasonic waves to the subject 99, and may receive visible light, infrared light, or ultrasonic waves reflected from the subject 99. In this case, the subject information collector 400 may count a predetermined time in which visible light, infrared light or ultrasonic waves are emitted, reflected, and fed back to the subject information collector 400, and may transmit the counted information to the subject measurement module 530. The subject measurement module 530 may measure thickness of the subject 99 on the basis of the above counted time.

The subject information collector 400 may be arranged at a specific position at which information regarding the subject 99 may be properly acquired. For example, the subject information collector 400 may be mounted to the radiation emission module 120 including the radiation emitter 100. If the subject information collector 400 is a camera, the camera may be mounted to the radiation emission module 120 in a manner that the image capturing element is arranged to face the same direction as the radiation emission direction.

Figure 3:
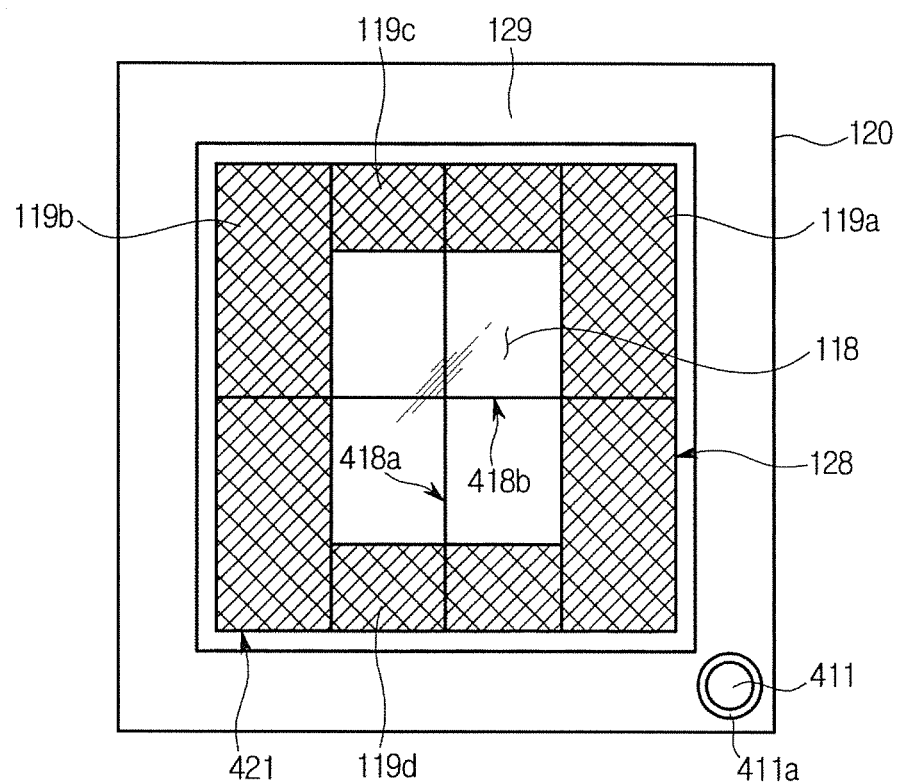
FIG. 3 illustrates a view of an external appearance of a radiation emission surface through which radiation of a radiation emission module is emitted.

Referring to FIG. 3, an opening 128 may be provided at any one of outer surfaces 129 from among a plurality of surfaces. The collimator 117 may be installed in the opening 128. All or some of the opening 128 may be shielded (or covered) by the collimator blades (119a to 119d), such that the size of a radiation emission outlet 118 (hereinafter referred to as an outlet) through which radiation generated by the radiation tube 111 is emitted.

The opening 128 may be sealed by a transmission plate 418, and the transmission plate 418 may be shaped in a planar plate formed of a radiation-transmissible material. Guide lines (418a, 418b) may be formed in the transmission plate 418. If light is emitted from a visible light source embedded in the radiation emission module 120, light and shade parts (contrast) of the guide lines (418a, 418b) may appear in a radiation emission region. Accordingly, the user may recognize the radiation emission region using the contrast result of the guide lines (418a, 418b).

The subject information collector 400 may be installed in the vicinity of the opening 128. In this case, the subject information collector 400 may be installed to receive visible or infrared light incident from the subject 99. In accordance with one embodiment, an exposure hole 411a may be provided at one outer surface 129 of a peripheral part of the opening 128, and a lens 411 of the subject information collector 400 may be exposed to the outside through the exposure hole 411a. The lens 411 exposed through the exposure hole 411a may focus incident light, for example, visible light, and may transmit the focused light to the image capturing element. As described above, the lens 411 of the subject information collector 400 is arranged to face the radiation emission direction in the vicinity of the opening 128 through which radiation is emitted, such that the subject information collector 400 may properly image the subject 99 to be irradiated.

The power-supply module 101, the radiation emitter 100, and the radiation detector 200 according to one embodiment will hereinafter be described in detail.

Figure 4:
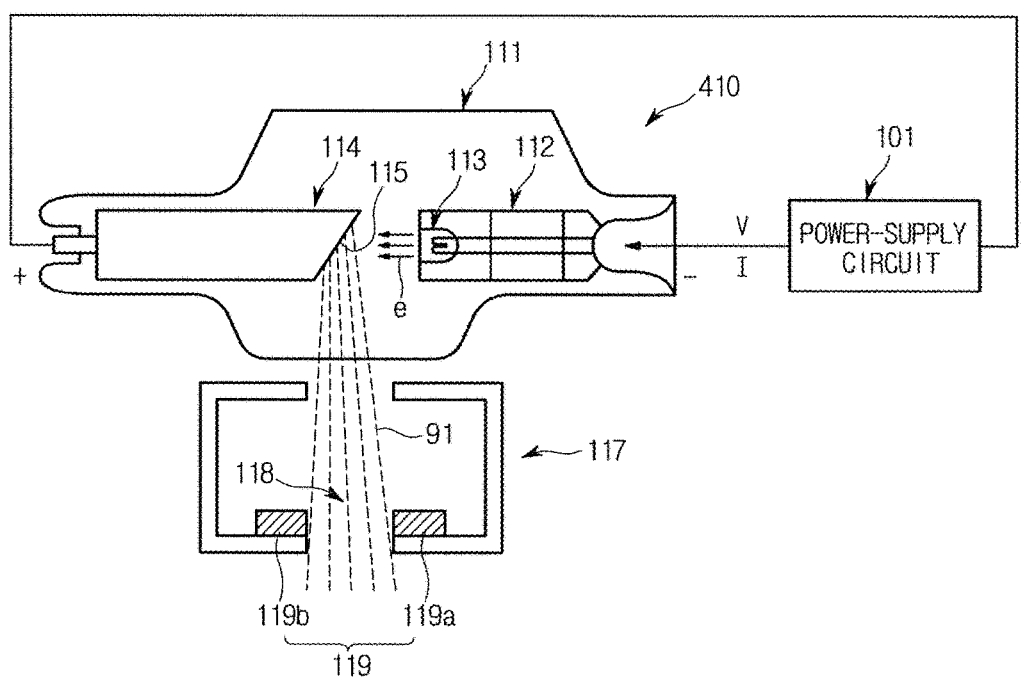
FIG. 4 illustrates a view of operations of a radiation emitter.

FIG. 4 illustrates a view of operations of the radiation emitter.

As described above, the power-supply module 101 may output electric energy having a predetermined tube voltage and a predetermined tube current to the radiation tube 111 of the radiation emitter 100. The radiation emitter 100 may emit radiation 91 having predetermined intensity and predetermined dose according to tube voltage and tube current of the electric energy received from the power-supply module 101.

In this case, intensity of radiation emitted from the radiation emitter 100 may be changed in response to the received tube voltage, and dose of radiation may be changed in response to the product of tube current and time. In this case, the dose of radiation emitted from the radiation emitter 100 may be measured in mAs. The power-supply module 101 may include a power-supplier configured to boost, reduce, or rectify commercial power received from the external part, or may include a battery configured to supply electric energy by generating electromotive force (EMF).

The radiation emitter 100 of the radiographic imaging module 10 may generate radiation having predetermined energy according to the received tube voltage and tube current, and may be disposed to emit the generated radiation in the direction of the subject 99.

In accordance with one embodiment, the radiation emitter 100 may include a radiation tube 111 to generate radiation 91 and a collimator 117 to adjust the range of the emitted radiation 91.

As can be seen from FIG. 4, the radiation tube 111 may include a tube body 111, a cathode 112, and an anode 114.

The tube body 111 may include various components such as the cathode 112 and the anode 114, may stably fix the cathode 112 and the anode 114 to the inside thereof, and may shield an electron beam (e) that occurs in the cathode 112 and moves to the anode 114 such that the electron beam (e) does not leak to the outside.

In the cathode 112, the electron beam (e) including a plurality of electrons may be emitted in the direction of the anode 114 upon receiving electric energy having a predetermined tube voltage (V) and a predetermined tube current (I) from the power-supply module 101. The tube voltage may denote a voltage applied to the radiation tube 111 or a circuit of the front end of the radiation tube 111, and the tube voltage may be measured in kVp or the like. The tube current may denote a current applied to the radiation tube 111 or the front end circuit of the radiation tube 111, and may be measured in mA or the like.

A filament 113 or a carbon nanotube may be provided in the cathode 112, and the filament 113 or the carbon nanotube may emit electrons having predetermined energy according to the tube voltage (V). The emitted electrons may move in the direction of the anode 114.

A target surface 115 may be provided at the anode 114, and predetermined radiation 91 may be emitted according to the occurrence of electrons colliding with the target surface 115. The radiation 91 emitted from the anode 114 may be emitted in the direction of the subject 99. The radiation 91 emitted from the target surface 115 may have energy corresponding to the received tube voltage (V).

In accordance with one embodiment, the anode 114 may include a fixed anode as shown in FIG. 4 or a rotation anode (not shown) shaped in a rotational circular plate.

In accordance with one embodiment, the collimator 117 may be installed in the progressing direction of the radiation 91 so as to adjust the radiation emission range. The collimator 117 may be configured to adjust the radiation emission range in a manner that the radiation proceeding in a specific direction passes through the collimator 117 and the other radiation proceeding in the remaining directions other than the specific direction is absorbed by the collimator 117.

Referring to FIGS. 3 and 4, the collimator 117 may be installed in the radiation emission module 120 in a manner that the collimator 117 is exposed in the radiation emission direction.

The collimator 117 may include a collimator blade 119. For example, the collimator blade 119 may be formed in a planar plate. For example, the collimator blade 119 may be formed of lead (Pb) capable of absorbing radiation. In accordance with one embodiment, the collimator 117 may include a plurality of collimator blades (119a to 119d), for example, four collimators (119a to 119d).

Referring to FIG. 3, the opening 128 may be provided at one outer surface 129 from among the plurality of surfaces of the radiation emission module 120. At least one collimator blades (119a to 119d) may be provided in the opening 128, and may be formed to shield all or some of the opening 128. Since all or some of the opening 128 is shielded by the collimator blades (119a to 119d), it may be possible to adjust the size of the outlet 118 through which the radiation generated by the radiation tube 111 is emitted. The outlet 118 through which the radiation 91 is emitted may be disposed among the first to fourth collimator blades (119a to 119d), and the size of the outlet 118 may be adjusted according to proximity movement or separation movement among the respective collimator blades (119a to 119d). As a result, the size of a radiation emission region of the subject 99 may be adjusted.

Figure 5:
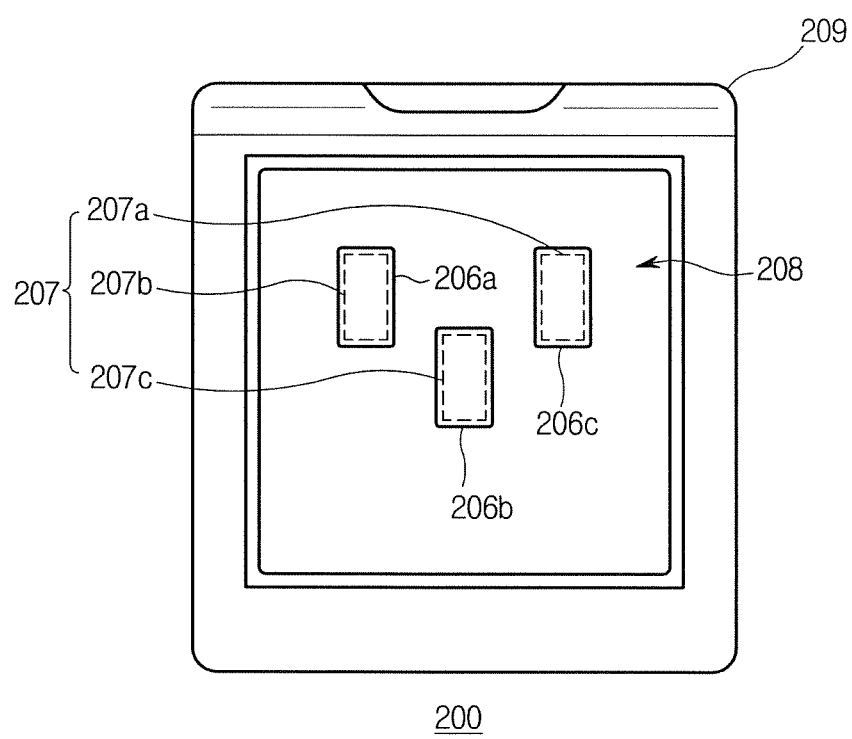
FIG. 5 illustrates a view of an external appearance of the radiation emission surface of the radiation emission module.

FIG. 5 illustrates a view of an external appearance of a radiation emission surface according to an embodiment of the present disclosure.

Referring to FIG. 5, the radiation detector 200 may include an anti-scattering grid 210 configured to prevent the scattered radiation from among the radiation 91 transmitted through the subject 99; and a radiation detection panel 220 configured to receive the radiation 91, convert the received radiation 91 into an electrical signal, and output the electrical signal.

As can be seen from FIG. 5, the radiation detector 200 may include a detector housing 209 configured to include various components of the radiation detector 200. The detector housing 209 may be inserted into at least one of the first radiation detector mounting module 22 and the second radiation detector mounting module 25, and mounted therein. An incident plate 208 on which radiation is incident may be provided at one surface of the detector housing 209. The anti-scattering grid 210 and the radiation detection panel 220 are stacked and installed in the incident plate 208.

While the radiation passes through the subject 99, the anti-scattering grid 210 may absorb the radiation scattered by the subject 99, the radiation 91 proceeding in an appropriate direction may pass through the anti-scattering grid 210, such that the radiation 91 proceeding in the appropriate direction may arrive at the radiation detection panel 220.

The radiation detection panel 220 may receive the radiation having transmitted through the anti-scattering grid 210, may convert the received radiation into an electrical signal, and may output the electrical signal.

In accordance with one embodiment, the radiation detection panel 220 may use the direct conversion scheme for directly converting radiation into an electrical signal, or may use the indirect conversion scheme for generating visible light based on radiation and converting the generated visible light into an electrical signal. In accordance with one embodiment, the radiation detection panel 220 may also generate the electrical signal using any one of a charge integration mode and a photon counting mode.

In accordance with one embodiment, a radiation sensor 207 may be dispose between the incident plate 208 and the anti-scattering grid 210.

The radiation sensor 207 may detect the dose of incident radiation, may output an electrical signal according to the detection result, and may transmit the electrical signal to the controller 500. The radiation sensor 207 may be implemented using, for example, an ionization chamber.

In accordance with one embodiment, the controller 500 may compare the radiation dose detection result with a predetermined threshold value. If the radiation dose is higher than the threshold value according to the result of comparison, automatic exposure control (AEC) in which the radiation emitter 110 automatically stops operation to prevent excessive exposure to radiation may be carried out.

In addition, according to one embodiment, the controller 500 may store the radiation dose detection result in the database 610 of the storage module 600. In this case, the database 610 may store the radiation dose detected by the radiation sensor 207 along with various kinds of information regarding the subject 99, for example, length, width, or thickness of the subject 99, intensity of incident radiation 91, and dose of the radiation emitted by the radiation emitter 110.

The radiation sensor 207 may include a plurality of radiation sensors, for example, first to third radiation sensors (207a to 207c). Each of the first to third radiation sensors (207a to 207c) may independently detect the dose of radiation. The respective radiation sensors (207a to 207c) may be installed in some regions of the detector housing 209. For example, two radiation sensors (207a, 207b) may be installed at an upper end of the detector housing 209, and only one radiation sensor 207c may be installed at a lower end of two radiation sensors (207a, 207b). In this case, markers (206a, 206b, 206c) for respectively indicating the positions of the sensors (207a to 207c) may be marked on the incident plate 208 of the detector housing 209. The respective markers (206a, 206b, 206c) may be provided to correspond to the respective radiation sensors (207a to 207c), and the positions of the respective markers (206a, 206b, 206c) may be disposed on the incident plate 208 in response to the positions of the corresponding radiation sensors (207a to 207c).

The operations of the controller 500 will hereinafter be given.

Figure 6:
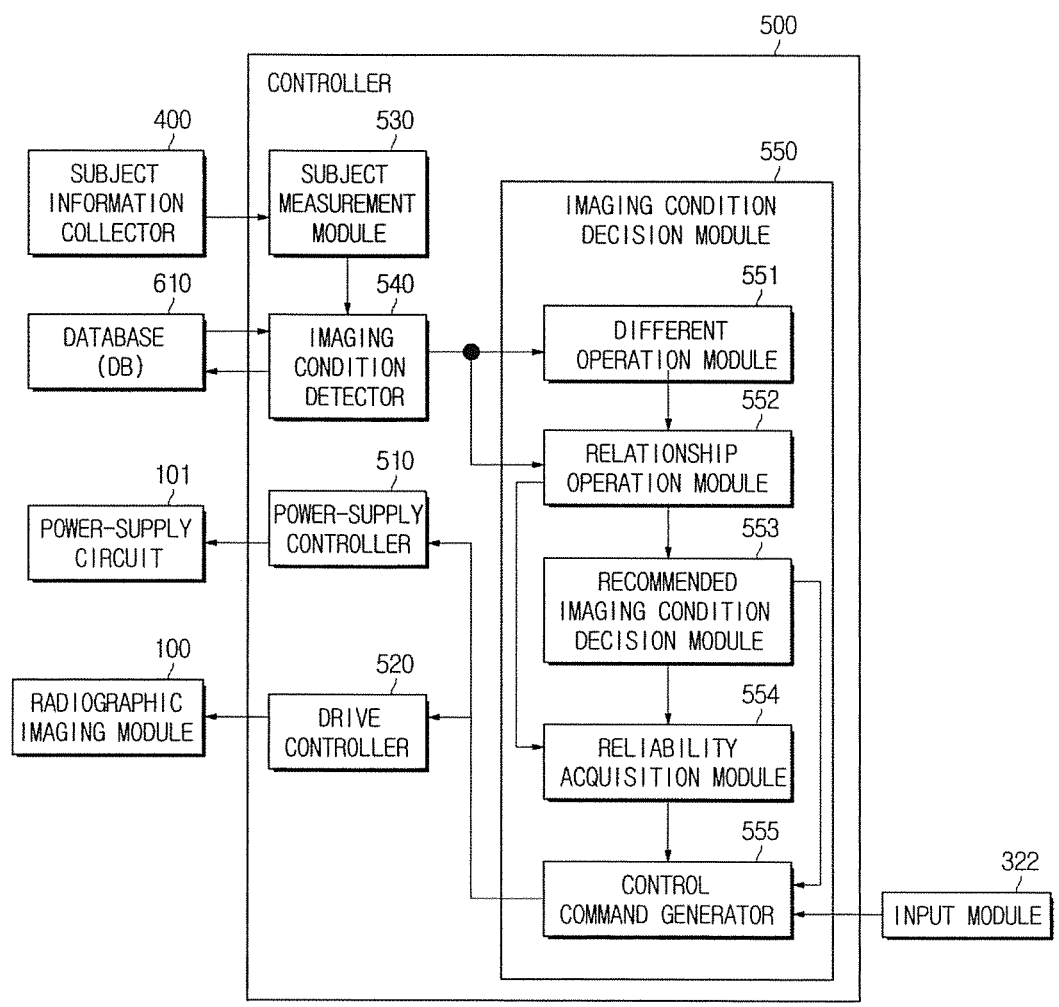
FIG. 6 illustrates a block diagram of a controller according to an embodiment of the present disclosure.

FIG. 6 illustrates a block diagram of a controller according to an embodiment of the present disclosure.

Referring to FIG. 6, the controller 500 may include a power-supply controller 510, a drive controller 520, a subject measurement module 530, and an imaging condition detector 550.

The power-supply controller 510 generates a control signal according to the imaging condition decided by the imaging condition decision module 550, transmits the control signal to the power-supply module 101, and transmits electric energy corresponding to the imaging condition to the radiation tube 111 of the radiation emitter 100. In this case, the imaging condition may include the size of a tube voltage corresponding to radiation intensity and the product of time and a tube voltage corresponding to the dose of radiation. The power-supply module 101 may supply electric energy to the radiation tube 111 according to the received tube voltage and the product of time and tube current.

The drive controller 520 may generate a control signal according to either a user command entered through the input module 322 of the user interface (UI) 320 or the imaging condition decided by the imaging condition decision module 550, may transmit the control signal to at least one of the radiation emitter 100 and the radiation detector 200, and may control the at least one of the radiation emitter 100 and the radiation detector 200 to be operated according to user intention or the decided imaging condition. In more detail, the drive controller 520 may control at least one of the radiation emitter 100 and the radiation detector 200 to move from one place to another place as well as to change the progressing direction to another direction according to the user intention or the decided imaging condition.

The subject measurement module 530 may be provided to measure the size of the subject 99 to be imaged. In more detail, the subject measurement module 530 may receive the image from the subject information collector 400, and may measure the size of the subject 99 to be imaged using the received image. In this case, the size of the subject 99 may include at least one of length, width, and thickness of the subject 99. If the subject 99 to be imaged is a human body, the size of the subject 99 may include various numerical values capable of being measured, for example, the height, shoulder width, and chest breadth of the human body.

In accordance with one embodiment, the subject measurement module 530 may determine the length or width of the subject 99 using the length of the subject 99 contained in the image and the distance between the subject information collector 400 and the subject 99. In addition, the subject measurement module 530 may also determine the length or width of the subject 99 using an indicator (e.g., a graduated ruler) indicating the size of the subject 99.

In addition, the subject measurement module 530 may measure thickness of the subject 99 on the basis of a time period in which visible light, infrared light, or ultrasonic waves transmitted from the subject information collector 400 are reflected and return to the subject measurement module 530. In this case, the subject measurement module 530 may measure the distance between the subject information collector 400 installed in the radiation emission module 120 and the subject 99 on the basis of the time period in which visible light, infrared light, or ultrasonic waves are reflected and return to the subject measurement module 530, and may measure thickness of the subject 99 not only using the distance between the radiation emission module 120 and the detector housing 209 of the radiation detector 200, but also using the distance between the subject information collector 400 and the subject 99. In this case, the distance between the radiation emission module 120 and the detector housing 209 in which the radiation detector 200 is installed may be determined on the basis of the moving directions and the moving distances of the radiation emitter 100 and the radiation detector 200 under the control of the drive controller 520, or may be acquired by measuring the distance between the subject information collector 400 and the detector housing 209 using the subject information collector 400.

In accordance with one embodiment, the imaging condition detector 540 may search for subject information similar to the subject 99 to be imaged in the database 610 stored in the storage module 600, and may detect the imaging condition according to the search result.

FIG. 7 illustrates a view of examples of subject information and various imaging conditions stored in the database. FIG. 8 illustrates a view of an example for detecting the imaging condition corresponding to second subject information obtained from the database.

Referring to FIG. 7, the database 610 may be constructed not only using information (hereinafter referred to as first subject information) regarding at least one subject (hereinafter referred to as a first subject) previously imaged, but also using the imaging condition information previously used for imaging of the first subject. In this case, if the subject is human, the first subject information may include at least one of age, sex, race, length, thickness, and width of the subject, and may further include various kinds of data considered by the system designer. In addition, the imaging condition may include not only the value of a tube current used when the first subject is imaged, but also the dose of radiation absorbed by the first subject and detected by the radiation detector 200. If necessary, the imaging condition may further include the value of a tube voltage measured when the first subject is imaged. The imaging condition may further include various kinds of data related to the subject imaging according to designer intention.

If the first subject is imaged, the database 610 may store information regarding the imaged first subject and information regarding the imaging condition obtained when the first subject is imaged, in a manner that the imaged first subject information is stored to be matched to the imaging condition information. In other words, if information regarding the first subject is detected, the database 610 may integrate the first subject information and the imaging condition obtained when the first subject is imaged, and may store the integrated resultant information as a single database record (any one of 611 to 614). As a result, if the first subject information is detected, the imaging condition used when the first subject is imaged can also be detected. If the first subject information and the imaging condition used when the first subject is imaged are stored as a single database record (any one of 611 to 614), a separate identification (ID) code for identifying the first subject may be added to the database record (any one of 611 to 614).

If a plurality of first subjects is imaged, the database 610 may include a plurality of database records (611 to 614) corresponding to the plurality of first subjects. In the same manner as described above, the respective database records (611 to 614) may include the first subject information and the imaging condition information, and may further include an ID number for identifying the respective database records (611 to 614) as necessary.

If the user inputs information (hereinafter referred to as second subject information) regarding a currently imaged subject 99 (hereinafter referred to as a second subject) through the subject information input module 323, the imaging condition detector 540 may detect the database records (612, 613), each of which includes the first subject information, from among the plurality of database records (611 to 614) as illustrated in FIG. 8. Here, the database records (612, 613) may be entered from among the plurality of database records (611 to 614), or may include first subject information that is identical or similar to the second subject information acquired from among the plurality of database records (611 to 614). In this case, the second subject information may include, for example, age, sex, race, and size (height) of the second subject. In addition, even when the subject measurement module 530 measures and acquires information regarding the size of the second subject, the imaging condition detector 540 may detect the database records (612, 613), each of which includes the first subject information, from among the plurality of database records (611 to 614) as illustrated in FIG. 8. Here, the database records (612, 613) may be entered from among the plurality of database records (611 to 614), or may include first subject information that is identical or similar to the second subject information acquired from the plurality of database records (611 to 614).

In this case, the imaging condition detector 540 may compare the second subject entered or acquired with data stored in each field of each database record (611 to 614). If a difference between the second subject information and the data stored in each field of specific records (612, 613) is set to zero "0" or is in a predetermined range, the specific database records (612, 613) may be determined to be database records, each of which includes the first subject information that is identical or similar to the second subject information that is entered or acquired, such that the specific database records (612, 613) are detected as the database records. In this case, the field compared with the second subject information may be a field corresponding to the second subject information. In other words, if the second subject information is the age item, the field of the database records (611 to 614) may also denote the age items.

In addition, when the entered or acquired second subject information is compared with data stored in the fields of respective database records (611 to 614), assuming that some fields of the database records are identical or similar to each other and a difference in the remaining fields other than the some fields exceeds a predetermined range such that the remaining fields are different from each other, the imaging condition detector 540 may detect the database records (611 to 614) using various methods.

For example, if the number of fields identical or similar to the second subject information within the specific database records (612, 613) is higher than the number of fields different from the second subject information within the specific database records (612, 613), the imaging condition detector 540 may determine that specific database records (612, 613) are database records including first subject information identical or similar to the input or acquired second subject information. In another example, the imaging condition detector 540 may calculate a difference between the second subject information and data stored in each of the database records (612, 613), may calculate the sum of the calculated differences, and may determine whether the sum value is less than a predefined value. If the sum value is less than the predefined value, it may be determined that each of specific database records (612, 613) may be a database record including first subject information identical or similar to the input or acquired second subject information. In this case, the imaging condition detector 540 may add a weight to some parts of the calculated difference, and may detect specific database records (612, 613). For example, the imaging condition detector 540 may add a weight to a specific field (e.g., thickness of the subject) so as to detect specific database records (612, 613).

For example, under the condition that the database 610 may include first to fourth database records (611 to 614), if the second subject's age entered by the user is 42, the second subject's sex entered by the user is a female, the second subject's race entered by the user is Mongolian, the second subject's height entered by the user is 162 cm, and the second subject's thickness entered by the user is 25, the imaging condition detector 540 may detect a second database record 612 and a third database record 613, each of which includes first subject information identical or similar to the user-entered information regarding the second subject. In this case, the imaging condition corresponding to first subject information of each of the second database record 612 and the third DB record 613 may also be detected. For example, the detected imaging condition may include tube voltages (A2, A3), tube currents (B2, B3), and doses (C1, C3) obtained after radiation has passed through the subject.

The detected database records (612, 613) (i.e., not only first subject information, that is detected from the database 610 and is identical or similar to those of the second subject, but also the imaging condition corresponding to the first subject) may be transmitted to the imaging condition decision module 550.

In accordance with one embodiment, the imaging condition detector 540 may also detect first subject information and the imaging condition corresponding to the first subject using the imaging protocol. In more detail, the imaging condition detector 540 may further detect a protocol identical or similar to the imaging protocol to be used for imaging the second subject, from among a plurality of protocols used for imaging the first subject, such that the imaging condition detector 540 may detect not only the first subject information regarding the first subject, which is detected in the database 610 and identical or similar to the second subject, but also the imaging condition corresponding to the first subject.

The imaging condition decision module 550 may determine a recommended imaging condition using field information of each of the detected database records (612, 613), and may determine reliability of each recommended imaging condition. For example, the imaging condition decision module 550 may determine a recommended tube current and reliability of the recommended tube current using field information of each of the database records (612, 613). In addition, the imaging condition decision module 550 may also determine a recommended tube voltage and reliability of the recommended tube voltage.

Referring to FIG. 6, the imaging condition decision module 550 may include a difference operation module 551, a relationship operation module 552, a recommended imaging condition decision module 553, a reliability acquisition module 554, and a control command generator 555. The imaging condition decision module 550, the difference operation module 551, the relationship operation module 552, the recommended imaging condition decision module 553, the reliability acquisition module 554, and the control command generator 555 may be logically separated from one another or may be physically separated from one another.

The difference operation module 551 may calculate a difference between the first subject information and the second subject information. In this case, the difference operation module may subtract a data value of the second subject information (corresponding to each data value of the first subject information) from each data value of the first subject information, or may calculate a norm between each data value of the first subject information and a data value of the second subject information corresponding to each data value, such that the different operation module 551 may calculate a difference between the first subject information and the second subject information. The calculated difference between the first subject information and the second subject may be transferred to the imaging condition decision module 550. In accordance with one embodiment, the difference operation module 551 may be omitted as necessary.

The relationship operation module 552 may determine a recommended imaging condition and reliability of the recommended imaging condition using the relationship between the first subject information and transmittance, or may determine a recommended imaging condition and reliability of the recommended imaging condition using the relationship between transmittance and the difference (received from the difference operation module 551) between the first subject information and the second subject information.

If the difference between the first subject information and the second subject information is calculated by the difference operation module 551, the relationship operation module 552 may determine a recommended imaging condition and reliability of the recommended imaging condition using the relationship between transmittance and the difference between the first subject information and the second subject information.

If the difference operation module 551 is omitted, the relationship operation module 552 may determine a recommended imaging condition and reliability of the recommended imaging condition using the relationship between the first subject information and the transmittance, instead of using the relationship between the difference between the first subject information and the second subject information and the transmittance.

Here, the transmittance may be acquired by the following equation 1.

$$A = \frac{EI}{ESE} \quad \text{[Equation 1]}$$

In Equation 1, A may denote a transmittance, and EI may denote an exposure index. That is, EI may denote the dose of radiation having passed through the subject, and ESE may denote the abbreviation of an Entrance Skin Exposure indicating the dose of radiation acquired before the radiation passes through the subject. The dose of radiation acquired before the radiation passes through the subject may denote the dose of radiation emitted from the radiation emitter 100. The dose of radiation emitted from the radiation emitter 100 may correspond to a tube current applied to the radiation tube 111.

In Equation 1, the transmittance (A) may be defined as the ratio of EI (indicating the dose of radiation having passed through the subject) to ESE (indicating the dose of radiation acquired before radiation passes through the subject), as represented by $$A = \frac{EI}{ESE}.$$

In the meantime, ESE acquired before radiation passes through the subject may be calculated by the following equation 2.

$$ESE = f_{exposure}(V, I) \quad \text{[Equation 2]}$$

In Equation 2, V is a tube voltage, and I is a tube current. f_exposure(o) is a function for calculating the dose of radiation based on the tube voltage or the dose of radiation based on the tube current. f_exposure(o) may be experimentally or empirically obtained, or may also be acquired by theoretical operation.

As described above, the transmittance (A) may be defined as the ratio of EI (indicating the dose of radiation having passed through the subject) to ESE (indicating the dose of radiation acquired before radiation passes through the subject). EI and ESI may also be obtained using data stored in the database 610. In more detail, EI indicating the dose of radiation having passed the subject may be obtained using exposure indexes (C1, C2, C3) obtained through the radiation sensor 207 and stored in the database 610. ESE indicating the dose of radiation acquired before radiation passes through the subject may be calculated and obtained not only by the tube voltage and tube current stored in the database 610 but also by the equation 2.

An exemplary case in which the imaging condition decision module 550 determines a recommended imaging condition and reliability of the recommended imaging condition using the relationship between the first subject information and the transmittance will hereinafter be given.

Figure 9:
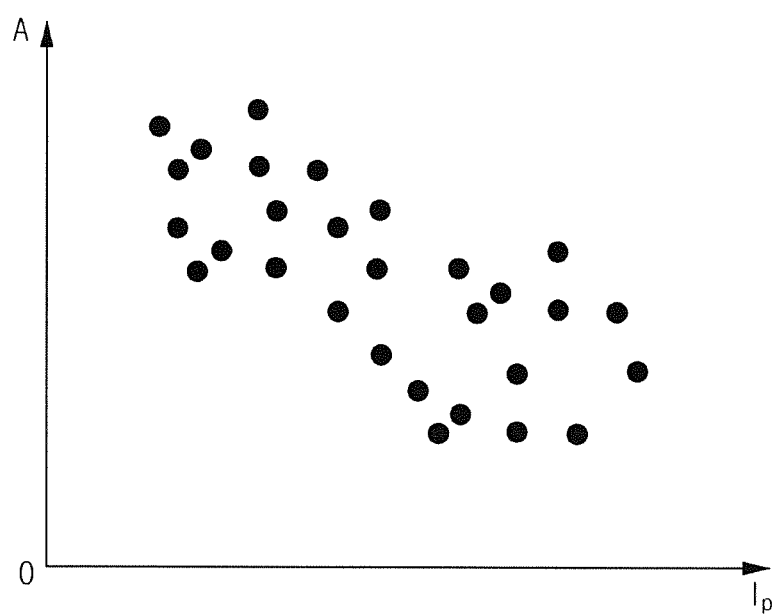
FIG. 9 illustrates a first graph of the relationship between first subject information and transmittance.
Figure 10:
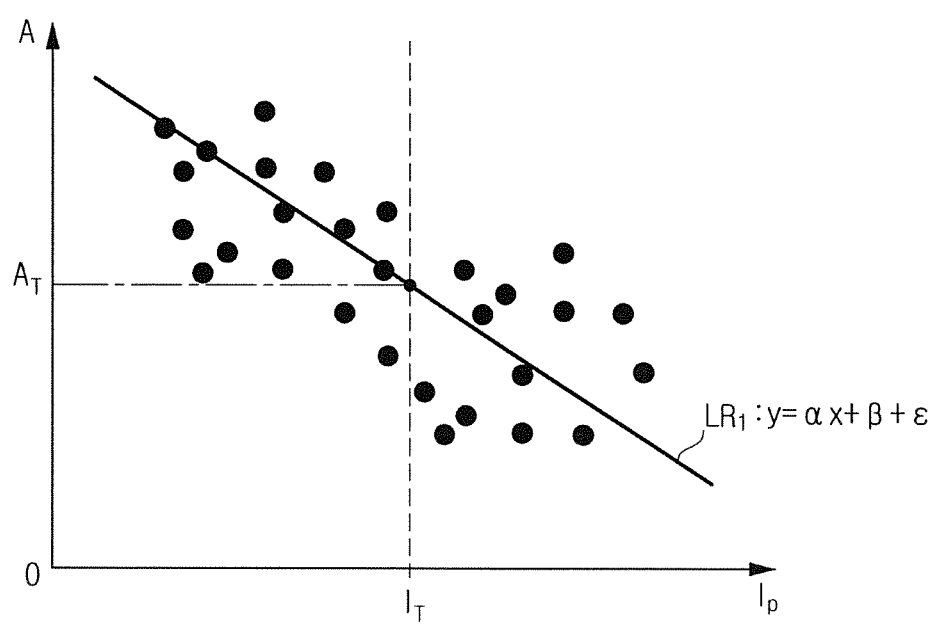
FIG. 10 illustrates a second graph of the relationship between first subject information and transmittance.
Figure 11:
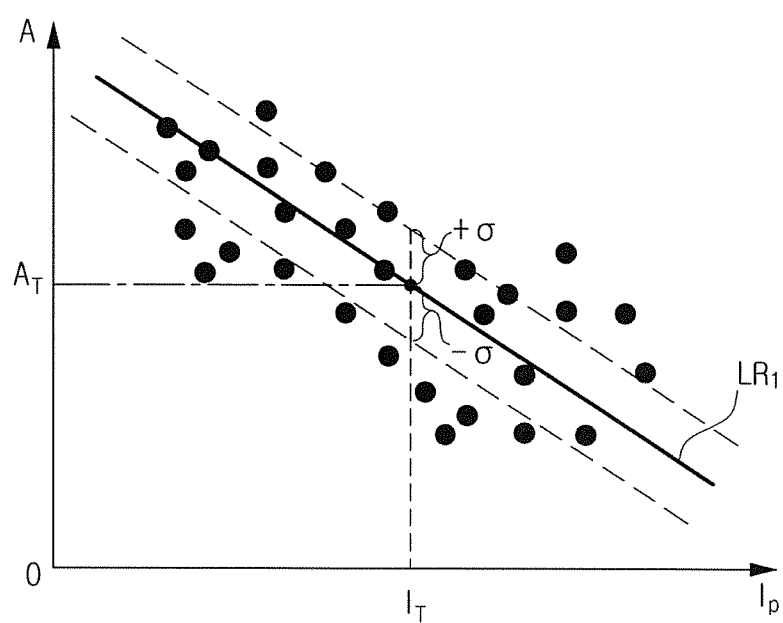
FIG. 11 illustrates a third graph of the relationship between first subject information and transmittance.

FIG. 9 illustrates a first graph of the relationship between first subject information and transmittance. FIG. 10 illustrates a second graph of the relationship between first subject information and transmittance. FIG. 11 illustrates a third graph of the relationship between first subject information and transmittance. In FIGS. 9 to 11, an X-axis may denote corrected first subject information and a Y-axis may denote transmittance.

As described above, at least one first subject information obtained by detecting at least one of the database records (611 to 614) contained in the database 610 may include at least two of a plurality of information pieces, for example, age, sex, and race of the subject, the length of the subject, thickness of the subject, and a width of the subject. To simplify the relationship between the first subject information and the transmittance, the first subject information may be converted into the corrected first subject information using the following equation 3.

$$I_p = f_p(x_1, x_2, x_3, \ldots, x_n)$$ [Equation 3]

In Equation 3, Ip may denote corrected first subject information, and fp(•) may denote a conversion function arbitrarily defined by the system designer. fp(•) may be implemented by a linear function or the like, or may also be implemented by an exponential or logarithmic function. x1, x2, x3, . . . xn may indicate a plurality of information pieces contained in the first subject information, for example, age, sex, and race of the subject, the length of the subject, and thickness or width of the subject. In this case, each of x1, x2, x3, . . . xn may be denoted by numerical values regarding different kinds of information.

As described above, assuming that a plurality of corrected first subject information pieces regarding a plurality of first subject information pieces is obtained, if the value of the plurality of corrected first subject information pieces is set to an X coordinate and a plurality of transmittance values corresponding to the respective first subject information pieces is set to a Y coordinate and both values are shown in a two-dimensional (2D) coordinate plane, the graph of FIG. 9 is obtained.

If a plurality of corrected first subject information pieces and a plurality of transmittances are present, regression analysis regarding the corrected first subject information and the transmittance may be carried out. That is, the relationship operation module 552 may perform regression analysis on the basis of first subject information and the transmittance corresponding to the first subject information, and may obtain the relationship between the first subject information and the transmittance corresponding to the first subject information.

In more detail, if the regression analysis is performed on the basis of the first subject information and the transmittance corresponding to the first subject information, the following equation 4 may be obtained.

$$y = \alpha x + \beta + \varepsilon$$ [Equation 4]

In Equation 4, x may denote first subject information, and y may denote transmittance. That is, x may denote the corrected first subject information. $\alpha$ may denote a slope of an acquired regression line. If x is set to zero "0", $\beta$ may denote a y-axis value. As illustrated in Equation 5, $\varepsilon$ may denote a predicted error of the regression line based on normal distribution in which a mean value is set to zero "0" and a dispersion value is set to $\sigma$.

$$\varepsilon \sim N(0, \sigma^2)$$ [Equation 5]

In Equation 5, the equation 4 obtained by executing the regression analysis using the first subject information and the transmittance may statistically indicate the relationship between the first subject information and the transmittance corresponding to the first subject information. The regression line (LR1) based on Equation 4 may pass through the spacing between a plurality of dots corresponding to the corrected first subject information and the transmittance.

The relationship operation module 552 may obtain information (e.g., the regression line LR1) regarding the relationship between the first subject information and the transmittance through the above-mentioned method, and may transmit information regarding the obtained first subject information and the transmittance to at least one of the recommended imaging condition decision module 553 and the reliability acquisition module 554.

Upon receiving information regarding the relationship between the first subject information received from the relationship operation module 552 and the transmittance, the recommended imaging condition decision module 553 may determine a target transmittance (A_T) corresponding to the second subject information that is entered by the user or measured/obtained through the subject measurement module 530.

In more detail, if the equation 4 is acquired, the recommended imaging condition decision module 553 may determine a value (IT) corresponding to the acquired second subject information, may calculate transmittance corresponding to the value (IT) corresponding to the determined second subject information using the equation 4, and may determine the calculated transmittance to be a target transmittance (A_T). For example, as can be seen from FIG. 10, a Y-axis value of a specific point at which a line segment, that passes through a value corresponding to the second subject information and is perpendicular to an X-axis, meets the regression line (LR1), may be a target transmittance (A_T). In this case, the value (IT) corresponding to the second subject information may be the corrected second subject information that is calculated and obtained using the same method as in the equation 3.

In this case, the target transmittance (A_T) may be identical to or different from any one of the plurality of dots corresponding to the corrected first subject information and the transmittance illustrated in FIG. 10.

If the target transmittance (A_T) is determined, the recommended imaging condition may be calculated by the following equations 6 and 7. As an example for calculating the recommended imaging condition, a method for calculating the recommended tube current from among the recommended imaging conditions will hereinafter be described. Equation 1 may be rewritten by the following equation 6.

$$ESE_T = \frac{A_T}{EI_T} \quad \text{[Equation 6]}$$

In Equation 6, A_T may denote a target transmittance, ESE_T may denote a target dose of radiation before radiation passes through the subject, and EI_T may denote a target dose of radiation having passed through the subject.

If the target transmittance (A_T) is calculated as described above, the target transmittance (A_T) is divided by the target dose (EI_T) of radiation having passed through the subject such that the target dose (ESE_T) of radiation obtained before the radiation passes through the subject is obtained. In accordance with one embodiment, from among the plurality of EI values (indicating the doses of radiation having passed through the first subject) stored in the database 610, the target dose (EI_T) of radiation having passed through the subject may be set to one EI value obtained when the first subject identical or similar to the second subject is imaged. In accordance with another embodiment, from among the plurality of EI values stored in the database 610, a mean or intermediate value of EI values obtained when the plurality of first subjects each similar to the second subject may be calculated and obtained. In accordance with still another embodiment, the mean or intermediate value of EI values may also be entered by a user such as a radiologic technician.

If the target dose (ESE_T) of radiation obtained before the radiation passes through the subject is acquired, a tube current (IT) may be calculated using the following equation 7.

$$I_T = G(ESE_T, V_T, C_{filter}) \quad \text{[Equation 7]}$$

In Equation 7, I_T may denote a tube current, ESE_T may denote a target dose of radiation obtained before the radiation passes through the subject, V_T may denote a tube voltage of electric energy applied to the radiation tube 111, and C_filter may denote a filter correction value according to the filter type. The filter correction value may be used to calculate the tube current (I_T) by applying a filter formed of copper (Cu) or aluminum (Al) mounted to the front end of the radiation emission module 120 to the radiographic imaging process, and may be a given constant according to the filter type. The filter correction value may be determined according to a material or thickness of the filter. G(•) may be a function indicating the relationship among the dose obtained when radiation passes through the subject, a tube voltage, a filter correction value, and a tube current. G(•) may be experimentally or empirically obtained, or may also be acquired by theoretical operation.

The target dose (ESE_T) of radiation obtained before the radiation passes through the subject may be obtained by the above-mentioned equation 6. The tube voltage (V_T) may be entered by the user. In accordance with one embodiment, from among the plurality of tube voltages regarding the first subject stored in the database 610, the tube voltage used when the first subject identical or similar to the second subject is imaged may be used. In accordance with another embodiment, from among the plurality of tube voltages regarding the first subject stored in the database 610, a mean or intermediate value of the tube voltages used when the plurality of first subjects each similar to the second subject may be calculated and obtained. In accordance with still another embodiment, the filter correction value (C_filter) may be entered by the user, or may be determined by an electrical signal generated from the sensor configured to sense the filter type.

The tube current (I_T) determined as described above may be determined to be a recommended tube current, such that the recommended imaging condition may be determined. The recommended imaging condition such as the recommended tube current may be transferred to the control command generator 555.

The reliability acquisition module 554 may determine the reliability of the decided target transmittance (A_T) upon receiving information regarding the relationship between the first subject information and the transmittance from the relationship operation module 552.

In more detail, as shown in Equations 4 and 5, the predicted error ($\varepsilon$) regarding the regression line (LR1) according to the regression analysis result may be present. The predicted error ($\varepsilon$) may be in a predetermined range ($-\sigma \sim +\sigma$). In other words, as illustrated in FIG. 11, transmittance (i.e., a y-axis value) predicted for a predetermined x-axis value (i.e., I_T) may have a predetermined probability (for example, 95%) and be present in the range (y$-\sigma \sim$y$+\sigma$). That is, although the target transmittance (A_T) is determined by the recommended imaging condition decision module 553, the target transmittance (A_T) may have a predetermined value within the range (A_T$-\sigma \sim$A_T$+\sigma$) having a predetermined probability. The reliability acquisition module 544 may obtain the range (A_T$-\sigma \sim$A_T$+\sigma$) in which the transmittance (A_T), may determine the obtained range to be the reliability, and may obtain the determined range indicating the reliability.

In other words, the reliability acquisition module 554 may calculate the predicted error ($\varepsilon$), or may receive the predicted error ($\varepsilon$) from the recommended imaging condition decision module 553 and obtain the predicted error ($\varepsilon$). The reliability acquisition module 554 may determine the obtained predicted error ($\varepsilon$) to be the reliability, and may transmit the determined reliability to the control command generator 555.

An exemplary case in which the imaging condition decision module 550 determines a recommended imaging condition and the reliability of the recommended imaging condition using the relationship between the transmittance and the difference between the first subject information and the second subject information will hereinafter be given.

Figure 12:
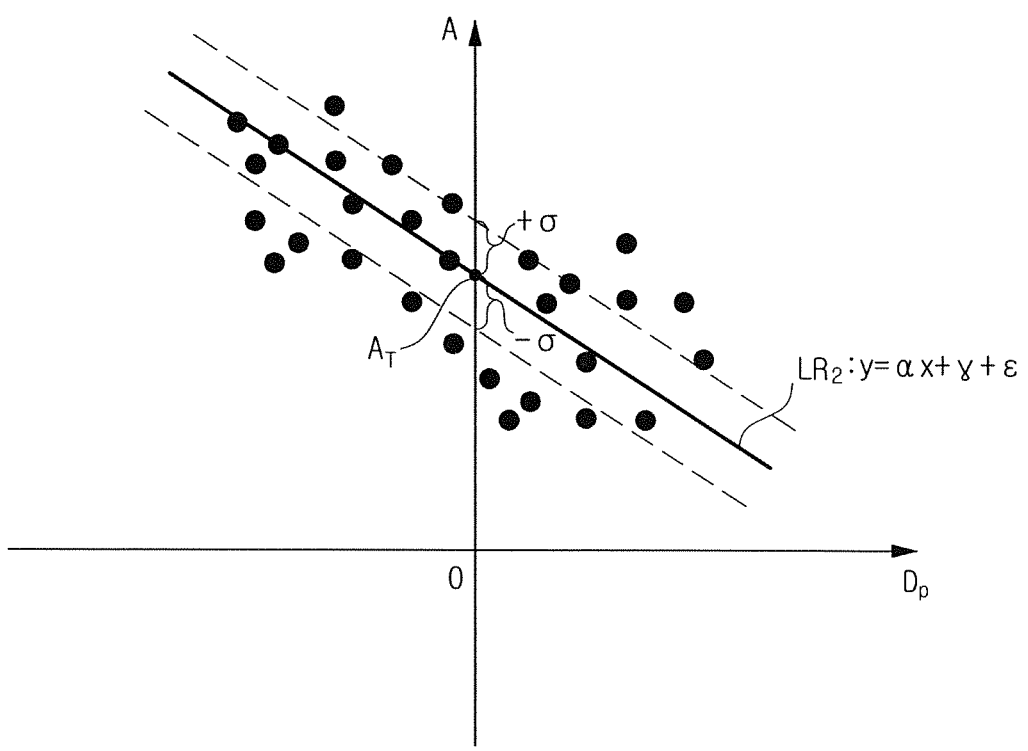
FIG. 12 illustrates a graph of the relationship between a difference between first subject information and second subject information and the transmittance.

FIG. 12 illustrates a graph of the relationship between a difference between first subject information and second subject information and the transmittance.

Referring to FIG. 12, the relationship operation module 552 may obtain the relationship between the transmittance and a difference between the first subject information and the second subject information using the above difference calculated by the difference operation module 551.

In this case, the difference operation module 551 may acquire the difference between the first subject information and the second subject information using the following equation 8.

$$Dp = I_{previous} - I_{current} \quad \text{[Equation 8]}$$

In Equation 8, D_p may denote a difference between the first subject information and the second subject information, I_previous may denote the first subject information, and I_current may denote the second subject information. In order to simplify the relationship between the subject information and the transmittance as shown in the equation 3, the difference between the first subject information and the second subject information may also be converted into a difference between the corrected first subject information and the second subject information.

In addition, the difference operation module 551 may acquire the difference between the first subject information and the second subject information using the following equation 9.

$$D_p = \|I_{previous} - I_{current}\|$$ [Equation 9]

In Equation 9, $\|\cdot\|$ may denote a norm, D_p may denote a difference between the first subject information and the second subject information in the same manner as in Equation 8. I_previous may denote the first subject information, and I_current may denote the second subject information. If the above-mentioned operation is achieved using the norm, the operation result need not be converted into the difference between the corrected first subject information and the second subject information.

If the difference between the first subject information and the second subject information is obtained by the difference operation module 551 as described above, the relationship operation module 552 may acquire the relationship between the transmittance and the difference between the first subject information and the second subject information. In this case, assuming that a plurality of differences between the first subject information and the second subject information and a plurality of transmittances are present as described above, the regression analysis regarding the transmittance and the difference between the first subject information and the second subject information may be carried out. In this case, the following equation 10 may be obtained.

$$y = \alpha x + \gamma + \varepsilon$$ [Equation 10]

In Equation 10, x may denote the difference between the first subject information and the second subject information, and y may denote the transmittance. α may denote a slope of the acquired regression line (LR2) as shown in FIG. 12. If x is set to zero "0", γ may denote a y-axis value. As illustrated in Equation 5, ε may denote a predicted error of the regression line based on normal distribution in which a mean value is set to zero "0" and a dispersion value is set to σ.

The relationship between the transmittance and the difference between the acquired first subject information and the second subject information may be transferred to at least one of the recommended imaging condition decision module 553 and the reliability acquisition module 554.

The recommended imaging condition decision module 553 may determine the recommended imaging condition in a similar way to the above description. In more detail, if the equation 10 is given according to the regression analysis result, the recommended imaging condition decision module 553 may obtain a Y-axis value at a specific point where an X-axis value is set to zero "0" and therefore there is no difference between the first subject information and the second subject information, such that the obtained Y-axis value may be determined to be the target transmittance (A_T). Subsequently, if the target transmittance (A_T) is decided, the recommended imaging condition, for example, the recommended tube current, may be determined in the same manner as described above. The determined recommended imaging condition may be transferred to the control command generator 555.

The reliability acquisition module 554 may obtain the reliability using the predicted error (?) of the regression line (LR2) in the same manner as described above. The obtained reliability may be transmitted to the control command generator 555.

As described above, assuming that the recommended imaging condition and the reliability are determined through the relationship operation module 552, the recommended imaging condition decision module 553, and the reliability acquisition module 554, or through the difference operation module 551, the relationship operation module 552, the recommended imaging condition decision module 553, and the reliability acquisition module 554, the control command generator 555 may receive the recommended imaging condition and the reliability, may generate a predetermined control command according to the received information, and may transmit the generated control command to at least one component of the radiographic imaging apparatus 1. For example, the control command generator 555 may generate a control command related to control, and may transmit the generated control command to at least one of the power-supply controller 510 and the drive controller 502. The control command generator 555 may generate a control command for controlling the display 321 of the user interface (UI) 320, and may transmit the generated control command to the display 321.

In accordance with one embodiment, the control command generator 555 may transmit a control signal to the power-supply controller 510 in a manner that electrical energy of the recommended tube current may be applied to the radiation tube 111 according to a recommended imaging condition (e.g., a recommended tube current). The power-supply controller 510 may generate a control signal corresponding to the received control signal, and may transmit the generated control signal to the power-supply module 101. Therefore, the power-supply module 101 may output a recommended tube current to the radiation tube 111, and the radiation tube 111 may emit the radiation 91 according to the recommended tube current. In this case, the dose of irradiated radiation may correspond to a tube current, such that the radiation 91 having a recommended dose corresponding to the recommended tube current may be emitted to the subject 99.

In accordance with another embodiment, the control command generator 555 may control the recommended imaging condition and the reliability to be displayed on the display 321 of the user interface (UI) 320.

The function for determining the recommended imaging condition and/or the reliability using the imaging condition detector 540 and the imaging condition decision module 550 may be carried out when a predetermined event occurs. Here, the predetermined event may occur when the user inputs a radiographic imaging request, when a relative position between the radiation emitter and the radiation detector is changed due to movement of at least one of the radiation emitter and the radiation detector, or when the second subject information is changed. Besides, the function for determining the recommended imaging condition and/or the reliability may also be carried out not only when the above-mentioned events occur but also when another event established by the designer or the user occurs.

For example, if an electrical order sheet is input to the radiographic imaging apparatus 1 through a wired communication network or a wireless communication network, the imaging condition detector 540 of the controller 500 may detect information regarding the first subject and associated imaging condition, and the imaging condition decision module 550 may determine a recommended imaging condition regarding the second subject 99 to be imaged using both first subject information and the associated imaging condition. Assuming that the subject measurement module 530 is used, the subject information collector 400 and the subject measurement module 530 may automatically or manually collect information regarding the subject 99 when any one of the above-mentioned events occurs, and may measure the size of the subject 99. Here, the events may include an event in which the user inputs a radiographic imaging request, an event in which a relative position between the radiation emitter and the radiation detector is changed, or an event in which the second subject information is changed.

Figure 13:
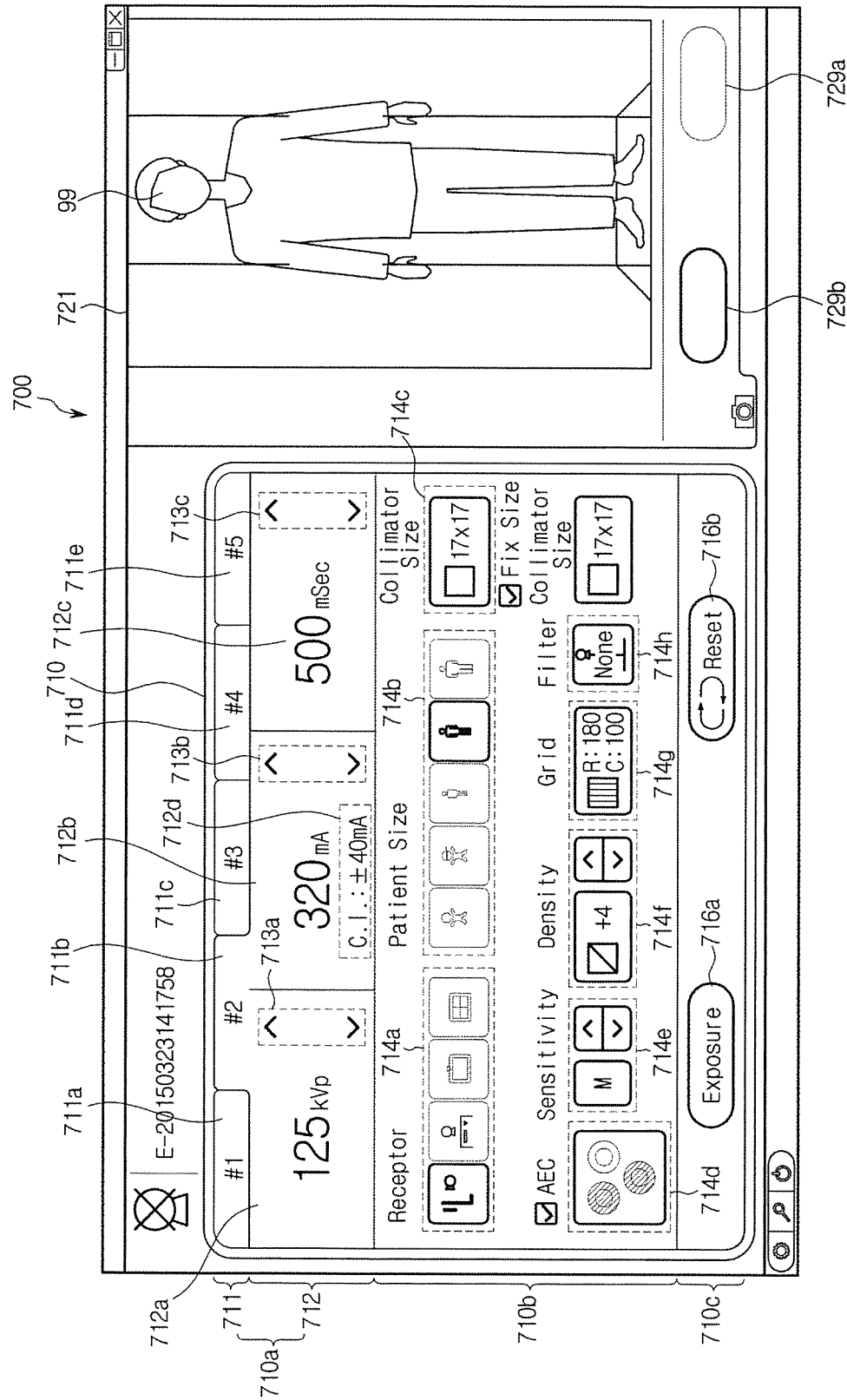
FIG. 13 illustrates a view of a first example of the screen image displayed on a display.

FIG. 13 illustrates a view of a first example of the screen image displayed on the display.

Referring to FIG. 13, a GUI 700 for assisting the user in a manner that the user can intuitively control the radiographic imaging apparatus 1 may be displayed on the screen image displayed on the display 321 according to a first example of the screen image displayed on the display shown in FIG. 13. In accordance with one embodiment, the GUI 700 may be implemented as a program window shown in FIG. 13 and displayed on the screen image, and the shape of the GUI 700 is not limited thereto, and the GUI 700 may be defined in various shapes considered by the designer.

The GUI 700 may include a setting control region 710 and an information display region 721. Various setting values needed to control the radiographic imaging module 10 may be displayed on the setting control region 710, or the user may adjust the setting value through the setting control region 710. Images acquired through the radiographic imaging module 10 may be displayed on the information display region 721, various paths through which data is stored may be displayed on the information display region 721, or various other information may be displayed on the information display region 721.

A tab 711 for selecting any one of a plurality of study parts may be provided at an upper part 710a of the setting control region 710. Either information regarding a tube voltage, a tube current, and an exposure time corresponding to the selected study part, or the radiation emission control interface 712 for adjusting the above information may be provided at a lower end of the tab 711. The study part may denote the set (or aggregate) of correlated radiographic images from among the radiographic images imaged by the radiographic imaging module 10. The doctor or the radiologic technician may image the plurality of radiographic images to diagnose or analyze the subject 99, and the term "study" may denote the set (or aggregate) of the plurality of imaged radiographic images.

The user may move a current to any one (e.g., second tab 711b) of tabs (711a to 711e) and click the selected one tab 711b, or may touch any one tab 711b from among the plurality of tabs (711a to 711e) so as to select the tab 711b. If any one tab (711b) is selected, the radiation emission control interface 712 related to the study corresponding to the selected tab may be displayed at a lower end of the tab 711.

The radiation emission control interface 712 may include an information display part on which radiation emission related information is displayed, and a setting change part through which radiation emission related setting is changed. The information related to radiation emission may include the tube voltage display region 712a, the tube current display region 712b, and the exposure time display region 712c. The setting change part may include a tube voltage adjusting button 713a, a tube current adjusting button 713b, and an exposure time adjusting button 713c.

A recommended tube voltage or a user-established tube voltage may be displayed on the tub voltage display region 712a. A recommended tube current or a user-established tube current may be displayed on the tube current display region 712b. A radiation exposure time during which radiation is exposed to the subject 99 may be displayed on the exposure time display region 712c.

In accordance with one embodiment, if the tube voltage display region 712a displays a recommended tube voltage obtained through the above-mentioned process, and/or if the tube current display region 712b displays a recommended tube current obtained through the above-mentioned process, the reliability 712d of a recommended tube voltage and/or a recommended tube current may be displayed on the tube voltage display region 712a and/or the tube current display region 712b.

In more detail, as illustrated in FIG. 13, if the recommended tube current is displayed on the tube current display region 712b, the letters C.I. (Confidential Interval) indicating the reliability and numerical values (e.g., +−40 mA) indicating the reliability may be displayed. The user such as a radiological technician may confirm the recommended tube current and reliability 712d, and may determine whether the value of a tube current to be irradiated to the subject 99 will be accommodated or changed.

Meanwhile, if the recommended tube voltage may be displayed on the tube voltage display region 712a, and/or if the recommended tube current is displayed on the tube current display region 712b, the user may change a tube voltage and/or a tube current by clicking the tube voltage adjusting button 713a and the tube current adjusting button 713b, or by touching a display region on which the tube voltage adjusting button 713a and the tube current adjusting button 713b are displayed using a touch means such as a finger or touch pen. Therefore, the user may apply electrical energy of another tube voltage and/or another tube current, instead of the recommended tube voltage and/or the recommended tube current, to the radiation tube 111.

In addition, the user may change an exposure time by clicking the exposure time adjusting button 713c or by touching a display region of the exposure time adjusting button 713c.

In accordance with one embodiment, the tube voltage adjusting button 713a may include a button for increasing the tube voltage or a button for reducing the tube voltage. The tube current adjusting button 713b may include a button for increasing the tube current or a button for reducing the tube current. In addition, the exposure time adjusting button 713c may include a button for increasing the exposure time or a button for reducing the exposure time.

The setting change portion for changing various setting data related to the radiation detector 412 or the collimator 117 may be provided at the lower end of the radiation emission control interface 712 (i.e., at the intermediate part 710b of the setting control region 710). The setting change portion may be implemented as a shape composed of letters, symbols, etc. The user may select any one shape by moving a cursor to this shape and clicking the corresponding shape or by touching a desired shape. Therefore, various setting data related to the imaging action of the radiographic imaging module 10 may be changed.

For example, the setting change portion may include a button 714a for receiving the setting command related to execution position of the radiographic imaging action. The setting command related to the execution position of the radiographic imaging may include a command indicating whether the radiographic imaging action will be executed at the subject support or at the subject stand.

In addition, the setting change portion may include a button 714b for receiving a selection command regarding the size of the subject 99. If the size of the subject 99 is selected, the radiographic imaging condition corresponding to the selected size may be displayed on the graphical user interface (GUI) 700. The radiographic imaging condition corresponding to the size of the subject 99 may be stored in the database 610 of the storage module 610 as described above.

In addition, the setting change portion may include a button 714c for receiving the setting data related to the size of the collimator 117, a button 714d for selecting any one of the radiation sensors (207a to 207c), a button 714e for setting the sensitivity, a button 714f for setting the density, a button 714g for adjusting the size of an anti-scattering grid, and a button 714h for selecting whether or not the filter is used.

The above-mentioned setting change portions are only exemplary, some parts of the setting change portions may be omitted according to selection of the designer, and not only the some parts but also a portion for changing another setting may further be used.

An emission starting button 716a for receiving an initiation command for the radiographic imaging action, and a reset button 716b for receiving the pre-selected setting items may be displayed at the lower end 710c of the setting control region 710. In the same manner as described above, the user may start the radiographic imaging action or may initialize the setting items by moving the cursor to the emission starting button 716a or the reset button 716b and clicking the corresponding button, or by touching the display position of the above buttons (716a, 716b).

For example, the information display region 721 may be displayed at a side surface of the setting control region 710. Images obtained through the radiographic imaging module 10 or through the subject information collector 400 may be displayed on the information display region 721, and various paths through which data is stored or other various kinds of information may be displayed on the information display region 721.

The user who views information displayed on the information display region 721 may adjust the setting of the setting control region 710 or the setting of the information display region 721 by manipulating the input module 620. Alternatively, the user may change various setting menus related to the operation of the radiographic imaging apparatus 1 by touching or dragging some parts of the information display region 721.

At least one of the buttons (729a, 729b) for receiving various commands related to images displayed on the information display region 721 may further be displayed at the lower end of the information display region 721.

Figure 14:
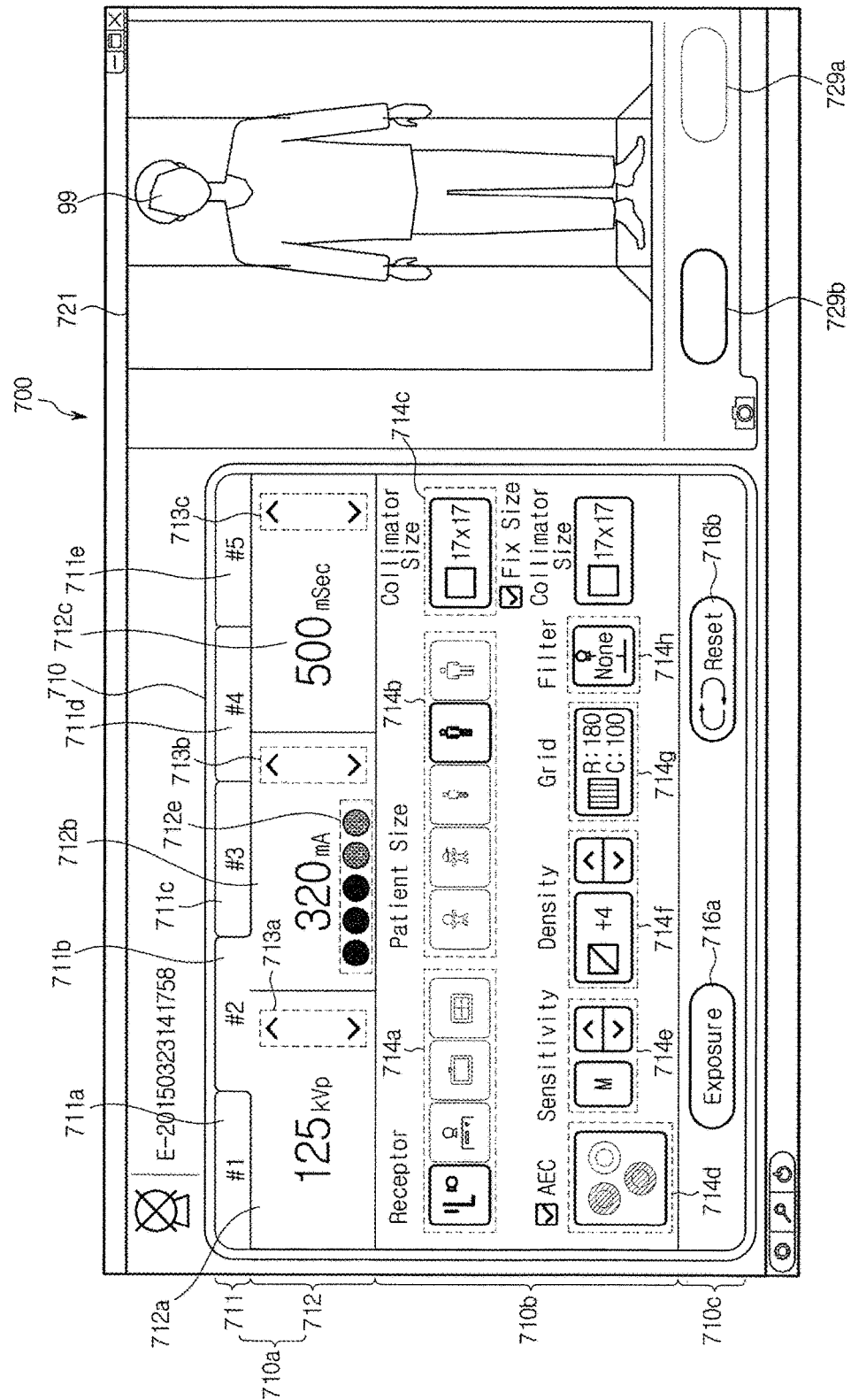
FIG. 14 illustrates a first view of a second example of the screen image displayed on a display.
Figure 15:
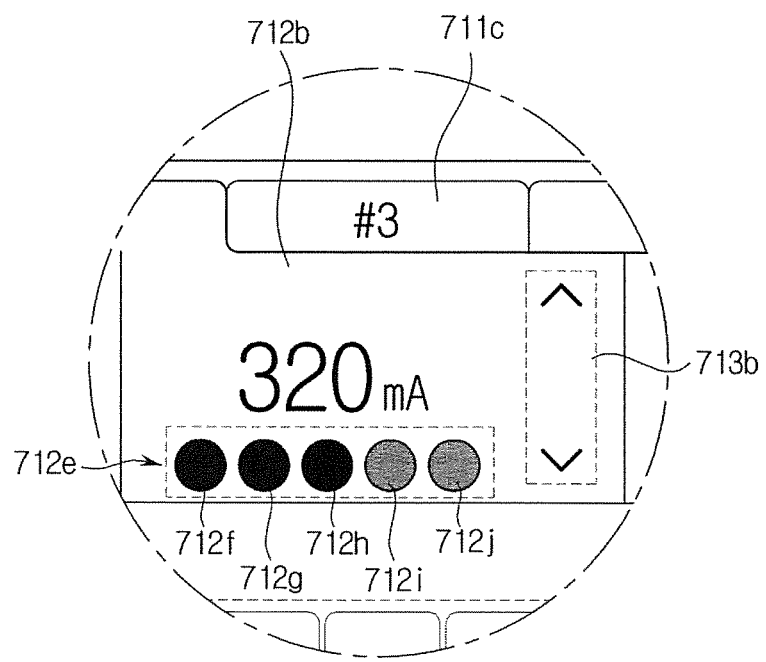
FIG. 15 illustrates a second view of a second example of the screen image displayed on a display.

FIG. 14 illustrates a first view of a second example of the screen image displayed on the display. FIG. 15 illustrates a second view of the second example of the screen image displayed on a display.

In accordance with the second example of the screen image displayed on the display shown in FIG. 14, a GUI 700 for assisting the user in a manner that the user can intuitively control the radiographic imaging apparatus 1 may be displayed on the screen image implemented by the display 321. In the same manner as described above, the GUI 700 may include a setting control region 710 and an information display region 721.

A plurality of tabs (711, 711a to 711e) for selecting any one of the plurality of study parts may be provided at the upper part 710a of the setting control region 710. Information regarding the tube voltage, the tube current, and the exposure time corresponding to the selected study or the radiation emission control interface 712 may be provided at the lower end of the tab 711.

The radiation emission control interface 712 may include a specific part on which the radiation emission related information (e.g., the tube voltage display region 712a, the tube current display region 712b, and the exposure time display region 712c) is displayed. The radiation emission control interface 712 may further include a radiation emission related setting change part through which the tube voltage adjusting button 713a, the tube current adjusting button 713b, and the exposure time adjusting button 713c may be changed. A recommended tube voltage or a tube voltage established by the user may be displayed on the tube voltage display region 712a, and a recommended tube current or a tube current established by the user may be displayed on the tube current display region 712b. The radiation exposure time during which radiation is exposed to the subject 99 may be displayed on the exposure time display region 712c.

In accordance with one embodiment, if the tube voltage display region 712a displays the recommended tube voltage acquired through the above-mentioned process, and/or if the tube current display region 712b displays the recommended tube current through the above-mentioned process, the reliability of 712e of the recommended tube voltage and/or the recommended tube current may be displayed as symbols or figures in the tube voltage display region 712a and/or the tube current display region 712b.

In this case, as illustrated in FIGS. 14 and 15, if the recommended tube current is displayed on the tube current display region 712b, the reliability may be displayed using the plurality of figures (712f to 712j). The reliability may be displayed by changing the shape or color of the plurality of figures (712f to 712j).

For example, each of the plurality of figures (712f to 712j) may be displayed in two or more colors. In this case, different reliability degrees of the recommended tube current (i.e., different reliabilities of the recommended tube current) may be supplied to the user according to display colors of the plurality of figures (712f to 712j). For example, in more detail, the plurality of figures (712f to 712j) becomes sequentially darker in color in the order from the left end to the right end of the figures (712f to 712j). For example, if the reliability is at a low reliability, relatively left-sided figures (712f, 712g) from among the plurality of figures (712f to 712j) may be displayed in the darkest color. If the reliability is at a high reliability, the right-sided figures (712i, 712j) from among the plurality of figures (712f to 712j) may be displayed in lighter colors. If the reliability is at the highest reliability, all of the figures (712f to 712j) may be displayed in dark colors.

As described above, the color or shape of the figures may be changed according to different reliability levels, reliabilities of the recommended imaging condition (i.e., the recommended tube voltage and/or the recommended tube current) may be displayed in a discrete (i.e., a state, function, or distribution that is not continuous) or scattered manner.

The user may intuitively determine the reliability of the recommended tube voltage and/or the reliability of the recommended tube current through colors or shapes, such that the user may determine whether the recommended tube voltage and/or the recommended tube current will be changed. If the user desires to change the recommended tube voltage and/or the recommended tube current, the user may input a new tube voltage and/or a new tube current, instead of the recommended tube voltage adjusting button 713a and/or the recommended current adjusting button 713b, using the tube voltage adjusting button 713a and/or the tube current adjusting button 713b.

The setting change portion for changing various setting menus related to the radiation detector 412 or the collimator 117 may be provided at the lower end of the radiation emission control interface 712. For example, the setting change portion may include a button 714a for receiving the setting command related to the execution position of the radiographic imaging action, a button 714b configured to receive a command for selecting the size of the subject 99, a button 714c for receiving the setting menu related to the size of the collimator 117, a button 714d for selecting any one of the plurality of radiation sensors (207a to 207c), a button 714e for setting the sensitivity, a button 714f for setting the density, a button 714g for adjusting the size of a grid, a button 714h for selecting whether or not the filter is used, etc.

As one embodiment of the radiographic imaging apparatus, the digital radiographic imaging apparatus has been disclosed as described above. However, the above-mentioned radiographic imaging apparatus is not limited to the digital radiographic imaging apparatus, and the above-mentioned radiographic imaging apparatus or its modification may also be applied to a mammography apparatus or a computed tomography (CT) apparatus without departing from the scope or spirit of the present disclosure. In addition, the above-mentioned radiographic imaging apparatus may also be applied to various devices capable of emitting radiation according to a specific imaging condition.

A method for controlling the radiographic imaging apparatus will hereinafter be described with reference to FIGS. 16 to 19.

Figure 16:
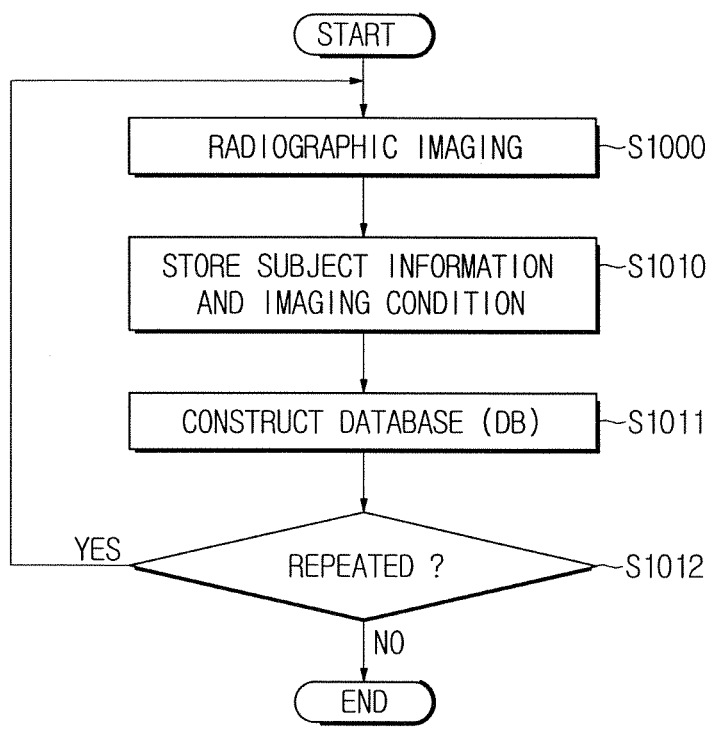
FIG. 16 illustrates a first flowchart of a method for controlling the radiographic imaging apparatus according to a first embodiment of the present disclosure.

FIG. 16 illustrates a first flowchart of a method for controlling the radiographic imaging apparatus according to a first embodiment of the present disclosure.

Referring to FIG. 16, the radiographic imaging for a specific subject may be carried out using a specific imaging condition, for example, a specific tube voltage and a specific tube current (S1000).

Prior to execution of the radiographic imaging, during the radiographic imaging, or upon completion of the radiographic imaging, information regarding the imaged subject and the imaging condition are stored in the storage module (S1010), such that a database in which the information regarding the imaged subject and the imaging condition are stored as database records may be constructed (S1011).

The above-mentioned operations S1000 to S1011 may be repeatedly carried out (S1012), such that the database comprised of information regarding at least one subject and the imaging condition corresponding to the subject is acquired.

Figure 17:
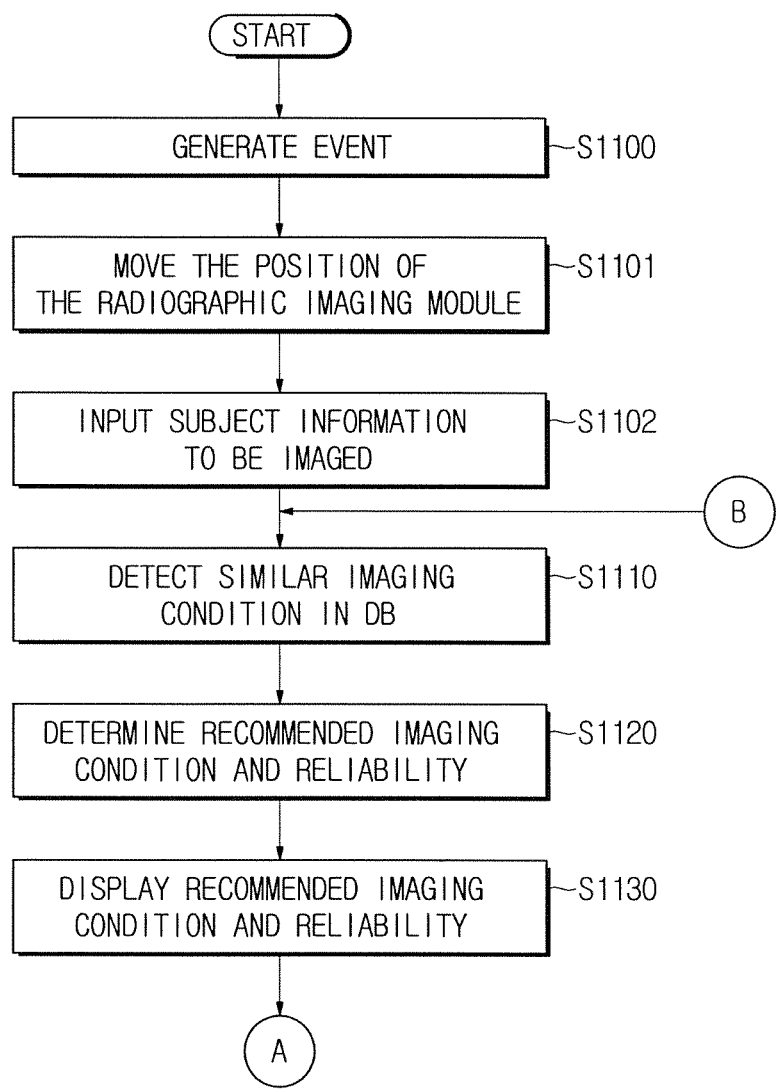
FIG. 17 illustrates a second flowchart of a method for controlling the radiographic imaging apparatus according to a first embodiment of the present disclosure.
Figure 18:
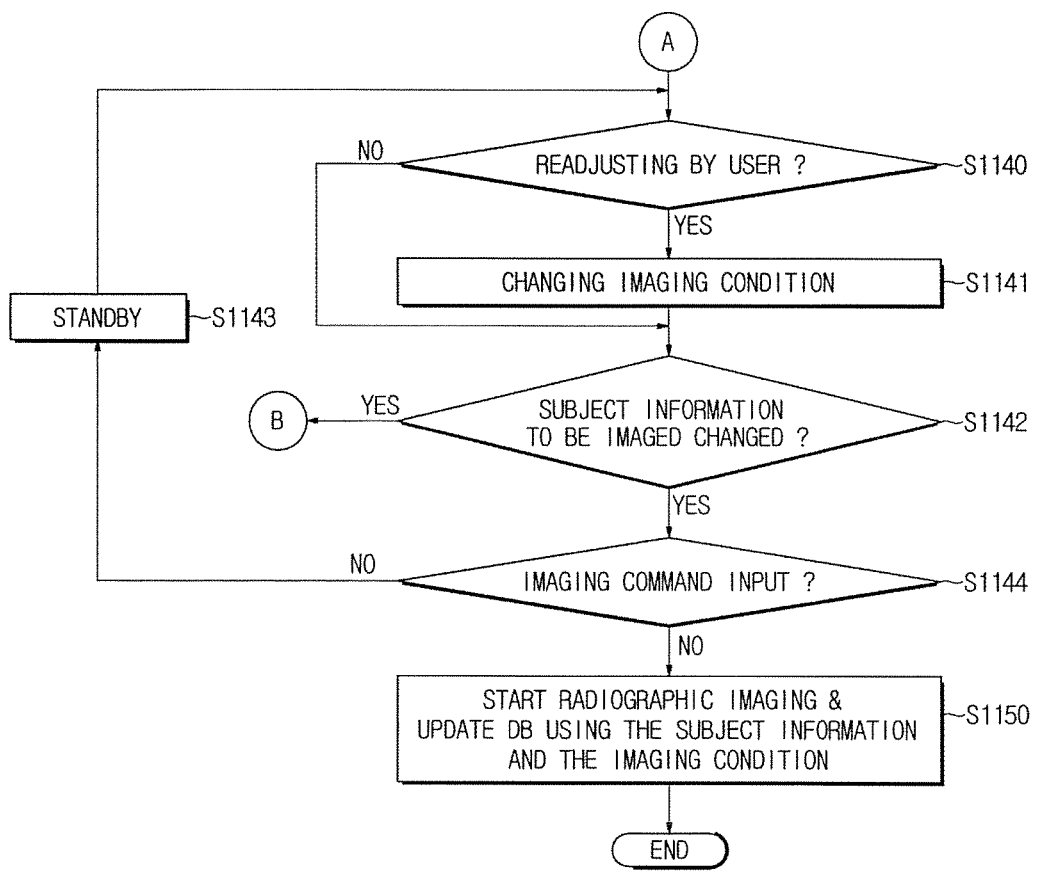
FIG. 18 illustrates a third flowchart of a method for controlling the radiographic imaging apparatus according to a first embodiment of the present disclosure.

FIG. 17 illustrates a second flowchart of a method for controlling the radiographic imaging apparatus according to a first embodiment of the present disclosure. FIG. 18 is a third flowchart illustrating a method for controlling the radiographic imaging apparatus according to a first embodiment of the present disclosure.

Referring to FIG. 17, after the database is acquired and stored in the storage module of the radiographic imaging apparatus, a predefined event may occur (S1100). In this case, the predefined event may include at least one of an input of the radiographic imaging request, change of relative positions of the radiation emitter and the radiation detector, and change of the second subject information. Besides, the predefined event may include various events according to selection of the designer or the user.

If the radiographic imaging request is input, at least one of the radiation emitter and the radiation detector contained in the radiographic imaging module may start moving to a specific position at which all or some parts of the subject can be properly imaged (S1101). In this case, movement of at least one of the radiation emitter and the radiation detector may be manually carried out by the user, or may be automatically carried out by the controller of the radiographic imaging apparatus. The radiation emitter and the radiation detector may not move at all according to peripheral situations.

Information regarding the subject to be imaged, i.e., the second subject information, may be input to the radiographic imaging apparatus (S1102). If the radiation emitter and the radiation detector move to other places, the input of the second subject information may be carried out after movement of at least one of the radiation emitter and the radiation detector, may be carried out before movement of at least one of the radiation emitter and the radiation detector, or may be carried out while in motion of at least one of the radiation emitter and the radiation detector. In this case, the user may input the second subject information to the radiographic imaging apparatus using an input module such as a keyboard, or may input the second subject information to the radiographic imaging apparatus over a wired or wireless communication network. If the wired or wireless communication network is used, the radiographic imaging apparatus receives the electrical order sheet such that the second subject information may be input to the radiographic imaging apparatus. In addition, the second subject information may also be input to the radiographic imaging apparatus using a portable storage or puncturing card, etc.

If the second subject information is input to the radiographic imaging apparatus, the radiographic imaging apparatus may detect not only the pre-stored subject information (i.e., first subject information) identical or similar to the second subject information in the database, but also the imaging condition corresponding to the first subject information (S1110). In this case, the first subject information may include at least one of age, sex, and race of the subject, length of the subject, thickness of the subject, and width of the subject. The imaging condition may include at least one of radiation strength, dose of radiation, an exposure index, and entrance skin exposure (ESE).

In this case, the radiographic imaging apparatus may compare the second subject information with data stored in fields contained in each database record. If a difference between the second subject information and data stored in fields of a specific database record is zero or is in a predetermined range, it is determined that the specific database record is a database record including the first subject information identical or similar to the second subject information, and the specific database record is then detected. Alternatively, assuming that the number of fields identical or similar to the second subject information within a specific database record is higher than the number of field different from the second subject information, the radiographic imaging apparatus may determine that a specific database record is a database record including the first subject information identical or similar to the second subject information. Alternatively, the radiographic imaging apparatus may calculate differences between the second subject information and data pieces stored in respective fields of the specific database record, may calculate the sum of the calculated differences, and may determine whether the calculated sum is less than the predefined value. In addition, the radiographic imaging apparatus may determine that a specific database record including the first subject information identical or similar to the input or acquired second subject information. Besides, the radiographic imaging apparatus may detect not only the first subject information identical or similar to the second subject information, but also the imaging condition corresponding to the first subject information in various ways.

If the first subject information identical or similar to the second subject information and the imaging condition corresponding to the first subject information are detected, the radiographic imaging apparatus may determine the recommended imaging condition using the detected imaging condition, and may determine the reliability of the recommended imaging condition (S1120).

In accordance with one embodiment, the radiographic imaging apparatus may determine at least one of a recommended imaging condition and the reliability of the recommended imaging condition on the basis of the first subject information corresponding to the detected imaging condition. In this case, in order to determine at least one of the recommended imaging condition and the reliability of the recommended imaging condition, the relationship between the first subject information and the transmittance may be used.

The relationship between the first subject information and the transmittance may be acquired using the regression analysis based on the first subject information and the transmittance. The radiographic imaging apparatus may acquire a target transmittance corresponding to the second subject information on the basis of the relationship between the first subject information and the transmittance obtained by the regression analysis result, and may determine a recommended imaging condition (e.g., a recommended tube voltage or a recommended tube current) according to the target transmittance. In other words, the radiographic imaging apparatus may determine the recommended radiation strength and/or the recommended radiation dose using the target transmittance. In accordance with one embodiment, a filter correction value may further be used to determine the recommended radiation strength and/or the recommended radiation dose as necessary.

In addition, the radiographic imaging apparatus may obtain the predicted error regarding the target transmittance corresponding to the second subject information on the basis of the relationship between the acquired first subject information and the transmittance obtained by the regression analysis result, such that the radiographic imaging apparatus may further obtain the reliability of the recommended imaging condition.

In accordance with another embodiment, the radiographic imaging apparatus may determine at least one of the recommended imaging conditions and the reliability of the recommended imaging condition on the basis of the difference between the first subject information and the second subject information corresponding to the detected imaging condition. In this case, in order to determine at least one of the recommended imaging condition and the reliability of the recommended imaging condition, the relationship between the transmittance and the difference between the first subject information and the second subject information may be used.

The relationship between the transmittance and the difference between the first subject information and the second subject information may be acquired using the regression analysis in the same manner as described above. The radiographic imaging apparatus may obtain a target transmittance corresponding to the second subject information on the basis of the above-mentioned relationship between the transmittance and the difference between the first subject information and the second subject information obtained by the regression analysis result, and may determine the recommended imaging condition according to the target transmittance.

Likewise, the radiographic imaging apparatus may obtain the predicted error regarding the target transmittance corresponding to the second subject information on the basis of the relationship between the transmittance and the difference between the first subject information and the second subject information obtained by the regression analysis result, and may determine the obtained predicted error to be the reliability of the recommended imaging condition.

If the recommended imaging condition and reliability are obtained, the obtained recommended imaging condition and reliability may be displayed on the display of the user interface (UI) for user recognition (S1130).

In this case, the recommended imaging condition may be displayed using letters or numbers and unit symbols corresponding to the imaging conditions. The reliability of the recommended imaging condition may be displayed using at least one of letters, numbers, symbols, and figures. In accordance with one embodiment, the display may also display reliability levels of the recommended imaging conditions in a discrete or scattered manner. For example, as shown in FIGS. 14 and 15, reliability levels of the recommended imaging conditions may be displayed through a plurality of figures, colors of all or some parts of the plurality of circles may be changed and displayed in other colors according to respective reliability levels, such that the reliability of the recommended imaging condition may also be displayed in a discrete or scattered manner.

If the recommended imaging condition and reliability are displayed on the display for user recognition, the user may confirm the recommended imaging condition and reliability, and may determine whether the radiographic imaging will be carried out according to the recommended imaging condition or according to another imaging condition instead of the recommended imaging condition.

If the user attempts to perform the radiographic imaging using another imaging condition instead of the recommended imaging condition, the user may adjust the imaging condition by manipulating the imaging condition change input module (e.g., a keyboard, a mouse, or a touchscreen) for changing the recommended imaging condition (S1140 'Yes')

If the user changes the imaging condition by manipulating the imaging condition change input module (S1140 'No'), various setting values (e.g., a tube voltage or a tube current) needed for radiographic imaging according to the changed imaging condition may be established (S1141).

If the user who desires to use the recommended imaging condition does not adjust the imaging condition (S1140 'No'), various numerical values (e.g., a tube voltage or a tube current) needed for radiographic imaging are established (S1141). In this case, prior to establishing various numerical values needed for radiographic imaging, the operation for allowing the user to enter an approval command of the radiographic imaging according to the recommended imaging condition may further be used.

If information regarding the second subject to be imaged on the condition that all the imaging conditions are established may be changed (S1142 'Yes'), first subject information and the imaging condition corresponding to the first subject information may be searched for in the database as described above (S1110).

The recommended imaging condition is determined on the basis of the searched imaging condition, and the reliability is then determined (S1120). The recommended imaging condition and the reliability are displayed (S1130). The imaging condition may be determined according to the presence or absence of user manipulation (S1140), or may be changed to another imaging condition (S1141).

If information regarding the second subject to be imaged is not changed (S1140 'No') and the imaging command is input (S1142 'Yes'), the radiographic imaging apparatus may perform the radiographic imaging of the second subject. In this case, prior to execution of the radiographic imaging of the second subject, during the radiographic imaging of the second subject, or after completion of the radiographic imaging of the second subject, information regarding the second subject and the imaging condition established to image the second subject are stored such that a database can be updated (S1150).

If the imaging command is not input (S1142 'No'), the radiographic imaging apparatus may enter a standby mode without any operation until the user inputs a specific command (e.g., the imaging condition change command or the subject information change command) in operation S1143.

Figure 19:
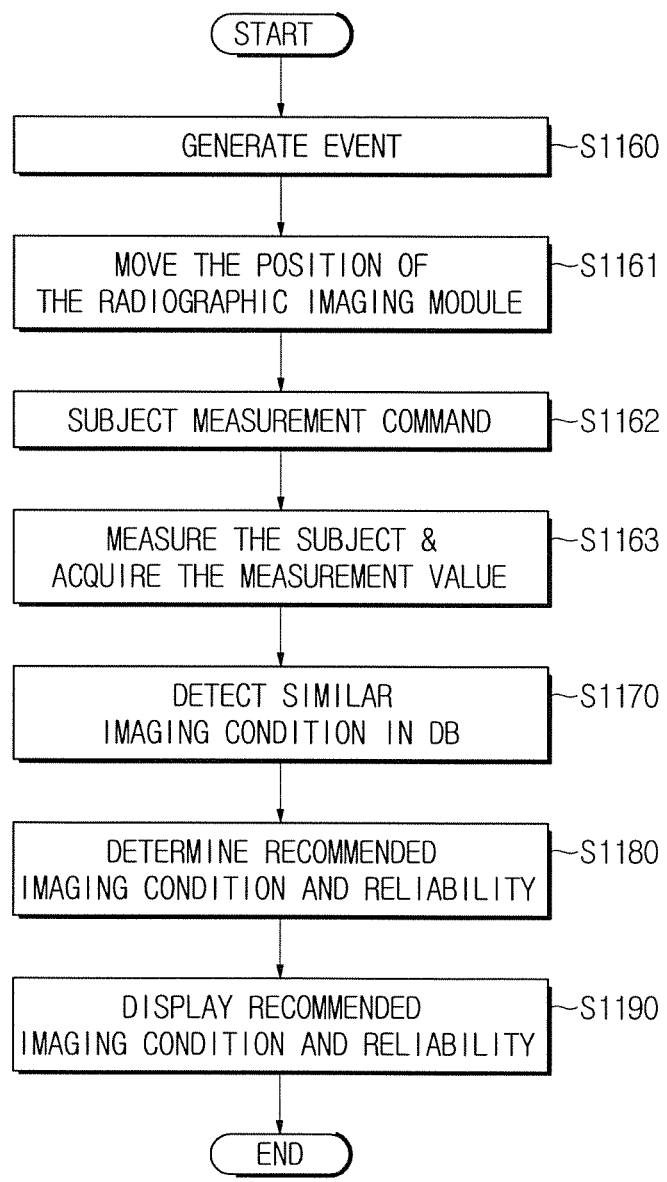
FIG. 19 illustrates a flowchart of a method for controlling the radiographic imaging apparatus according to a second embodiment of the present disclosure.

FIG. 19 illustrates a flowchart of a method for controlling the radiographic imaging apparatus including a subject information collector and a subject measurement module.

Referring to FIG. 19, any one of the predefined events may occur (S1160). In this case, the predefined event may include at least one of an input of the radiographic imaging request, change of relative positions of the radiation emitter and the radiation detector, and change of the second subject information.

Thereafter, at least one of the radiation emitter and the radiation detector contained in the radiographic imaging module may move to a specific position at which all or some parts of the subject can be properly imaged according to user manipulation or automatic control of the controller (S1161). In accordance with the situations, the radiation emitter and the radiation detector may not move at all.

Subsequently, the user may input a second subject measurement command (S1162). The inputting of the second subject measurement command may be carried out after movement of at least one of the radiation emitter and the radiation detector, may be carried out before movement of at least one of the radiation emitter and the radiation detector, or may be carried while in motion of the radiation emitter and the radiation detector. In accordance with one embodiment, the second subject measurement command may be automatically generated by the controller according to the predefined setting.

The radiographic imaging apparatus may measure at least one of various information pieces (e.g., the length, thickness, and width of the second subject) of the second subject to be imaged, according to the subject measurement command, and may obtain the measurement value regarding the second subject according to the measured result.

If the measurement value for the second subject is obtained, the radiographic imaging apparatus may read the database, and may detect information (i.e., the first subject information) regarding the first subject corresponding to the second subject and the imaging condition corresponding to the first subject information (S1170). The radiographic imaging apparatus may detect the first subject information and the imaging condition using only the measurement value regarding the second subject, and may detect the first subject information and the imaging condition using both the measurement value of the second subject and user-input information (e.g., age or sex of the second subject).

If the first subject information and the imaging condition are detected, the radiographic imaging apparatus may determine the recommended imaging condition from the detected imaging condition, and may determine the reliability of the recommended imaging condition (S1180).

If the recommended imaging condition and the reliability of the recommended imaging condition are obtained, the acquired recommended imaging condition and the reliability are displayed on the display (S1190).

Detailed description of the above-mentioned operations (S1170 to S1190) has already been disclosed and as such a detailed description thereof will herein be omitted for convenience of description.

The acquired recommended imaging condition and the reliability are displayed on the display, and the operations (S1140 to S1150) may further be carried out in the same manner as in FIG. 18.

The above-mentioned method for controlling the radiographic imaging apparatus disclosed in the embodiments of the present disclosure may be implemented in the form of programs executable by a variety of computer means. In this case, the program may include program commands, data files, data structures, etc. individually or in combination. Here, the program may include, for example, high-level language codes executable by a computer using an interpreter as well as machine language codes generated by a complier. In addition, the program may be particularly designed and configured to implement the above-mentioned method for controlling the radiographic imaging apparatus, or may also be implemented using various functions or definitions well known to those skilled in the art related to computer software.

The program for implementing the above-mentioned method for controlling the radiographic imaging apparatus according to embodiments of the present disclosure may be written in computer readable media. Examples of the computer readable media may include magnetic disc storage media, such as a hard disc or a floppy disc, and a magnetic tape, optical media, such as a compact disc (CD) and a digital versatile disc (DVD), magneto-optical media, such as a floptical disc, and hardware devices, such as semiconductor storage units (e.g., a read only memory (ROM), a random access memory (RAM), and a flash memory), which are particularly configured to store and execute specific programs executed by computers or the like.

As is apparent from the above description, the radiographic imaging apparatus and the method for controlling the same according to the embodiments can allow a user to properly establish imaging conditions needed for radiographic imaging.

The radiographic imaging apparatus and the method for controlling the same according to the embodiments can provide a user with not only a recommended value appropriate for intensity or dose of radiation but also reliability of the recommended value, such that the user may properly select the intensity or dose of radiation to be emitted on the basis of the recommended value and reliability thereof.

The radiographic imaging apparatus and the method for controlling the same according to the embodiments can allow a user to establish an optimum imaging condition needed for radiographic imaging according to unique characteristics (e.g., sex, age, race, and medical records) of various patients.

The radiographic imaging apparatus and the method for controlling the same according to the embodiments can allow a user who conducts anatomical programmed radiology (APR)-based radiographic imaging for patients, to more easily and quickly establish user-desired imaging conditions.

Although the above-mentioned embodiments of the present disclosure have been disclosed herein merely for illustrative purposes, the scope or spirit of the embodiments is not limited thereto, and those skilled in the art will appreciate that various modifications, additions and substitutions are possible, without departing from the scope and spirit of the disclosure as disclosed in the accompanying claims. For example, adequate effects of the present disclosure may be achieved even if the foregoing processes and methods may be carried out in different order than described above, and/or the aforementioned elements, such as systems, structures, devices, or circuits, may be combined or coupled in different forms and modes than as described above or be substituted or switched with other components or equivalents.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A radiographic imaging apparatus comprising:
   a database configured to store first subject information and an imaging condition corresponding to the first subject information;
   a controller, upon receiving second subject information regarding a subject to be imaged, configured to:
      detect an imaging condition corresponding to second subject information acquired from the database;
      determine a recommended imaging condition using the detected imaging condition; and
      determine reliability of the recommended imaging condition; and
   a user interface (UI) configured to display the recommended imaging condition and the reliability of the recommended imaging condition,
   wherein the controller is configured to determine at least one of the recommended imaging condition and the reliability of the recommended imaging condition based on a relationship between the first subject information and transmittance, or determine at least one of the recommended imaging condition and the reliability of the recommended imaging condition based on a difference between the transmittance and a difference between the first subject information and the second subject information.

2. The radiographic imaging apparatus according to claim 1, wherein the transmittance includes a ratio between a dose of radiation acquired before the radiation passes through the subject and a dose of radiation having passed through the subject.

3. The radiographic imaging apparatus according to claim 1, wherein the controller is configured to acquire a target transmittance using the second subject information, or acquire the target transmittance based on a difference between the first subject information and the second subject information, thereby determining the recommended imaging condition from the acquired target transmittance.

4. The radiographic imaging apparatus according to claim 3, wherein:
   the imaging condition corresponding to the first subject information includes radiation strength, and the recommended imaging condition includes a recommended dose of radiation; and
   the controller is configured to acquire the recommended dose of radiation using the target transmittance and the radiation strength corresponding to the first subject information.

5. The radiographic imaging apparatus according to claim 4, wherein the controller is configured to acquire the recommended dose of radiation using a filter correction value.

6. The radiographic imaging apparatus according to claim 3, wherein the controller is configured to acquire a predicted error regarding the target transmittance based on the relationship between the first subject information and the transmittance, or acquire the predicted error regarding the target transmittance based on the relationship between the transmittance and the difference between the first subject information and the second subject information, thereby determining the reliability of the recommended imaging condition.

7. The radiographic imaging apparatus according to claim 1, wherein the controller is configured to perform regression analysis based on the first subject information and the transmittance or perform the regression analysis based on the transmittance and the difference between the first subject information and the second subject information, thereby determining the relationship between the transmittance and the difference between the first subject information and the second subject information.

8. The radiographic imaging apparatus according to claim 1, wherein the user interface (UI) is configured to display the reliability of the recommended imaging condition using at least one of letters, numbers, symbols, or figures.

9. The radiographic imaging apparatus according to claim 1, wherein the user interface (UI) is configured to display the reliability of the recommended imaging condition in a discrete manner.

10. The radiographic imaging apparatus according to claim 1, wherein the imaging condition includes at least one of radiation strength, radiation dose, an exposure index (EI), or an entrance skin exposure (ESE).

11. The radiographic imaging apparatus according to claim 1, wherein:
   at least one of the first subject information and the second subject information includes at least one of age, sex, race of the subject, length of the subject, thickness of the subject, or width of the subject.

12. The radiographic imaging apparatus according to claim 1, further comprising
   a subject information collector configured to image a subject so as to measure at least one of length of the subject, thickness of the subject, or width of the subject.

13. The radiographic imaging apparatus according to claim 1, further comprising a subject information input module configured to receive at least one of length of a subject, thickness of the subject, or width of the subject.

14. The radiographic imaging apparatus according to claim 1, wherein the controller is configured to determine the recommended imaging condition and the reliability of the recommended imaging condition when a radiographic imaging request is input, when relative positions of a radiation emitter and a radiation detector are changed, or when the second subject information is changed.

15. The radiographic imaging apparatus according to claim 1, further comprising:
   an imaging condition change input module configured to change the recommended imaging condition.

16. A method for controlling a radiographic imaging apparatus comprising:

acquiring second subject information regarding a subject to be imaged;

detecting an imaging condition corresponding to the second subject information from a database for storing first subject information and an imaging condition corresponding to the first subject information;

determining a recommended imaging condition and reliability of the recommended imaging condition using the detected imaging condition; and displaying the recommended imaging condition and the reliability of the recommended imaging condition, wherein determining the recommended imaging condition and the reliability of the recommended imaging condition is based on:
- a relationship between the first subject information and transmittance, or
- a difference between the transmittance and a difference between the first subject information and the second subject information.

* * * * *